US008942852B2

(12) United States Patent
Tatsutani et al.

(10) Patent No.: US 8,942,852 B2
(45) Date of Patent: Jan. 27, 2015

(54) SAMPLE PROCESSING SYSTEM

(75) Inventors: Hiroo Tatsutani, Kobe (JP); Shunsuke Ariyoshi, Kobe (JP)

(73) Assignee: Sysmex Corporation, Kobe (JP)

( * ) Notice: Subject to any disclaimer, the term of this patent is extended or adjusted under 35 U.S.C. 154(b) by 169 days.

(21) Appl. No.: 13/448,900

(22) Filed: Apr. 17, 2012

(65) Prior Publication Data

US 2012/0269681 A1 Oct. 25, 2012

(30) Foreign Application Priority Data

Apr. 20, 2011 (JP) ................. 2011-094544

(51) Int. Cl.
*G01N 35/00* (2006.01)
*G01N 35/02* (2006.01)

(52) U.S. Cl.
CPC ........ *G01N 35/00722* (2013.01); *G01N 35/026* (2013.01); *G01N 2035/00891* (2013.01)
USPC ................. 700/266; 700/17; 700/83; 702/31; 702/32; 422/62

(58) Field of Classification Search
CPC .......... G01N 35/00722; G01N 35/026; G01N 2035/00891
USPC .............. 700/17, 266, 83; 702/31, 32; 422/62
See application file for complete search history.

(56) References Cited

U.S. PATENT DOCUMENTS

| 2009/0035867 | A1 | 2/2009 | Yagi et al. |
| 2010/0066996 | A1 | 3/2010 | Kosaka et al. |
| 2010/0093097 | A1 | 4/2010 | Kawamura |
| 2010/0254854 | A1* | 10/2010 | Rich et al. ........................ 422/64 |
| 2010/0287477 | A1 | 11/2010 | Maetzler et al. |

FOREIGN PATENT DOCUMENTS

| CN | 101358987 A | 2/2009 |
| CN | 101726617 A | 6/2010 |

* cited by examiner

*Primary Examiner* — Shogo Sasaki
(74) *Attorney, Agent, or Firm* — Brinks Gilson & Lione

(57) ABSTRACT

A sample processing system comprising: a sample processing apparatus configured to process a sample in a sample container; a transporting apparatus configured to transport a sample container to the sample processing apparatus; a first computer configured to perform information processing for the sample processing apparatus; a second computer connected to the first computer through a communication network and configured to control a transporting operation performed by the transporting apparatus; an input unit and a display commonly used for the first and second computers, wherein the first computer configured to control the display to show a first computer screen image, and to control the display to show a second computer screen image upon receiving a switching instruction via the input unit, and the second computer receives an input from the input unit via the second computer screen image shown on the display.

17 Claims, 16 Drawing Sheets

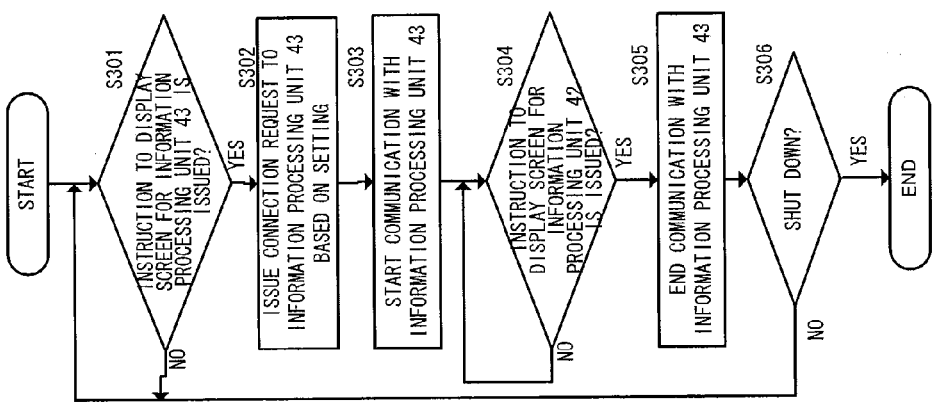
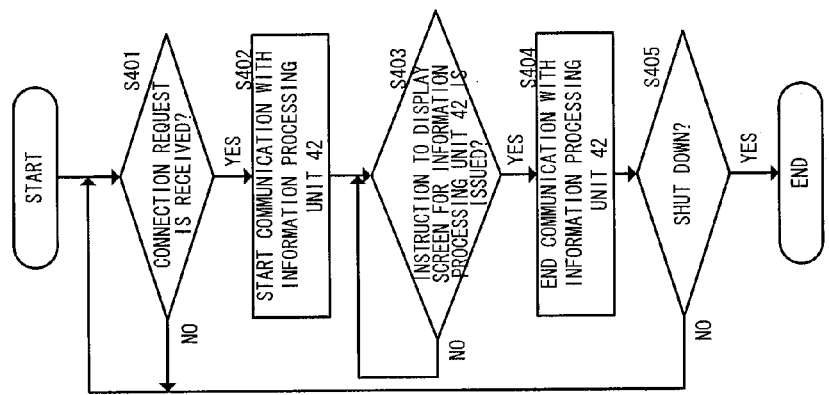

SAMPLE PROCESSING SYSTEM

RELATED APPLICATIONS

This application claims priority under 35 U.S.C. §119 to Japanese Patent Application No. 2011-094544 filed on Apr. 20, 2011, the entire content of which is hereby incorporated by reference.

BACKGROUND OF THE INVENTION

1. Field of the Invention

The present invention relates to a sample processing system that performs sample processing by use of a plurality of sample processing apparatuses.

2. Background of the Related Art

There have been known sample processing systems that transport samples to a plurality of sample processing apparatuses by means of transporting apparatuses.

For example, U.S. Patent Application Publication No. 2010/0066996 discloses a blood specimen analyzing system including: a host computer that manages measurement orders of samples; a plurality of measurement units that measure blood specimens; a specimen transporting apparatus that transports specimen containers to the measurement units; a system control apparatus that controls transporting operations of the specimen transporting apparatus based on measurement orders received from the host computer; an information processing unit that processes measurement data outputted from the measurement units, displays analysis results of the blood specimens, and transmits them to the host computer. Each of the information processing unit and the system control apparatus is provided with an input unit such as a keyboard to be operated by a user, an image display unit, and a computer. Each of the information processing unit and the system control apparatus is composed of a combination of the input unit, the image display unit, and the computer. Further, there is a case where a plurality of information processing units are provided in the system.

In a laboratory in which such an analysis system disclosed in U.S. Patent Application Publication No. 2010/0066996 is installed, there are cases where the information processing unit and the system control apparatus are not used by the user so often. In this case, with the blood specimen analyzing system according to U.S. Patent Application Publication No. 2010/0066996, there arises a problem that space in the laboratory is limited due to the input unit and the image display unit provided for each of the information processing unit and the system control apparatus, although they are not used so often.

The present invention has been made in view of the above problem. An object of the present invention is to provide a sample processing system that can effectively utilize space in a laboratory.

SUMMARY OF THE INVENTION

The scope of the present invention is defined solely by the appended claims, and is not affected to any degree by the statements within this summary.

A first aspect of the present invention is a sample processing system comprising: a sample processing apparatus configured to process a sample in a sample container; a transporting apparatus configured to transport a sample container to the sample processing apparatus; a first computer configured to perform information processing for the sample processing apparatus; a second computer connected to the first computer through a communication network and configured to control a transporting operation performed by the transporting apparatus; an input unit commonly used for the first and second computers; and a display unit commonly used for the first and second computers, wherein the first computer is capable of controlling the display unit to show a first computer screen image for the first computer, and is capable of controlling the display unit to show a second computer screen image for the second computer by connecting to the second computer through the communication network, the first computer controls the display unit to show the second computer screen image instead of the first computer screen image upon receiving a switching instruction via the input unit, and the second computer receives an input from the input unit via the second computer screen image shown on the display unit.

A second aspect of the present invention is a sample processing system comprising: a sample processing apparatus configured to process a sample in a sample container; a transporting apparatus configured to transport a sample container to the sample processing apparatus; a first computer configured to perform information processing for the sample processing apparatus; a second computer connected to the first computer through a communication network and configured to control a transporting operation performed by the transporting apparatus; an input unit commonly used for the first and second computers; and a display unit commonly used for the first and second computers, wherein the second computer is capable of controlling the display unit to show a second computer screen image for the second computer, and is capable of controlling the display unit to show a first computer screen image for the first computer by connecting to the first computer through the communication network, the second computer controls the display unit to show the first computer screen image instead of the second computer screen image upon receiving a switching instruction via the input unit, and the first computer receives an input from the input unit via the first computer screen image shown on the display unit.

A third aspect of the present invention is a sample processing system comprising: a plurality of sample processing apparatuses each configured to process a sample in a sample container; a first computer configured to perform information processing for at least a first sample processing apparatus among the plurality of sample processing apparatuses; a second computer connected to the first computer through a communication network and configured to perform information processing for at least a second sample processing apparatus which is different from the first sample processing apparatus among the plurality of sample processing apparatuses; an input unit commonly used for the first and second computers; and a display unit commonly used for the first and second computers, wherein the first computer is capable of controlling the display unit to show a first computer screen image for the first computer, and is capable of controlling the display unit to show a second computer screen image for the second computer by connecting to the second computer through the communication network, the first computer controls the display unit to show the second computer screen image instead of the first computer screen image upon receiving a switching instruction via the input unit, and the second computer receives an input from the input unit via the second computer screen image shown on the display unit.

A fourth aspect of the present invention is a sample processing system comprising: a sample processing apparatus configured to process a sample in a sample container; a transporting apparatus configured to transport a sample container to the sample processing apparatus; a plurality of computers connected to each other through a communication network and each configured to perform information processing for the sample processing system; an input unit commonly used for the plurality of computers; and a display unit commonly used for the plurality of computers, wherein a first computer among the plurality of computers is capable of controlling the display unit to show a first computer screen image for the first computer, and is capable of controlling the display unit to show a second computer screen image for a second computer among the plurality of computers through the communication network by connecting to a the second computer, when the first computer received a switching instruction via the input unit and the second computer is specified, the first computer controls the display unit to show the second computer screen image instead of the first computer screen image, and the second computer receives an input from the input unit via the second computer screen image shown on the display unit.

BRIEF DESCRIPTION OF THE DRAWINGS

FIG. 15A and FIG. 15B are flow charts showing processes performed by computer bodies of information processing units when screens are switched in a modification of a sample processing system according to an embodiment, respectively.

DETAILED DESCRIPTION OF THE PREFERRED EMBODIMENTS

The preferred embodiments of the present invention will be described hereinafter with reference to the drawings.

The present embodiment is realized by applying the present invention to a sample processing system for performing tests and analyses of blood. A sample processing system according to the present embodiment includes three measurement units and one smear preparing apparatus. The three measurement units perform blood analyses in parallel, and when preparation of smears is needed based on the analysis results, smears are prepared by the smear preparing apparatus.

Hereinafter, the sample processing system according to the present embodiment will be described with reference to the drawings.

Figure 1:
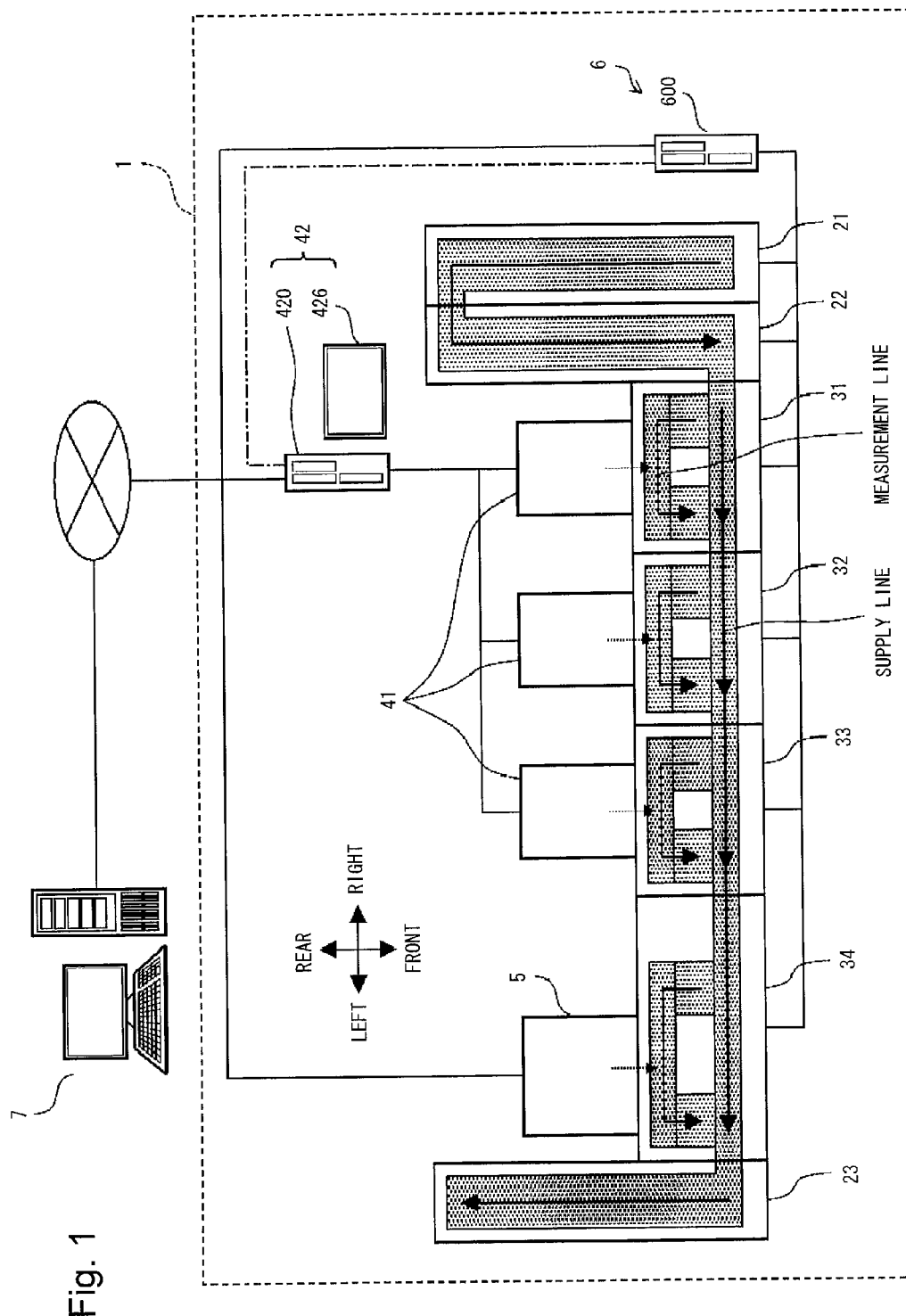
FIG. 1 schematically shows a configuration of a sample processing system according to an embodiment, viewed from above.

FIG. 1 schematically shows a configuration of a sample processing system 1, viewed from above. The sample processing system 1 according to the present embodiment includes a loading unit 21, a preprocessing unit 22, a collection unit 23, transporting units 31 to 34, three measurement units 41, an information processing unit 42, a smear preparing apparatus 5, and a transportation controller 6. Moreover, the sample processing system 1 of the present embodiment is communicably connected to a host computer 7 through a communication network.

The loading unit 21, the preprocessing unit 22, the transporting units 31 to 34, and the collection unit 23 are arranged in contact with their adjacent units as shown in FIG. 1, such that sample racks can be transported therebetween. Each of these units is configured such that a plurality of sample racks each capable of holding a plurality of sample containers can be placed therein.

The loading unit 21 accommodates sample racks loaded by a user, and transports the accommodated sample racks to the preprocessing unit 22. When starting measurement of a sample, the user sets a sample container containing a sample in a sample rack, and then places the sample rack on the loading unit 21. Then, the sample rack is sequentially transported to the downstream units (left side), and measurement is performed.

The preprocessing unit 22 receives the sample rack transported by the loading unit 21. By using a bar code unit (not shown), the preprocessing unit 22 reads a rack ID of the sample rack transported by the loading unit 21 and a sample ID of the sample container associated with a holder of the sample rack. Then, the preprocessing unit 22 transmits information read by the bar code unit to the transportation controller 6, and transports the sample rack for which the reading has been completed, to the transporting unit 31.

As shown in FIG. 1, the transporting units 31 to 33 are arranged to the front of the three measurement units 41, respectively, and the transporting unit 34 is located to the front of the smear preparing apparatus 5. Each of the transporting units 31 to 34 receives the sample rack transported by an adjacent unit located to the right thereof, and transports it to an adjacent unit located to the left thereof.

As shown in FIG. 1, each of the transporting units 31 to 33 is provided with two types of transportation lines, that is, one for a case where the sample rack is transported to its corresponding measurement unit 41, and the other for a case where the sample rack is not transported to its corresponding measurement unit 41. That is, when measurement is performed in a measurement unit 41, the sample rack is transported along a rear-located "measurement line" indicated by a U-shaped arrow. When measurement is not performed in the measurement unit 41 and measurement is performed or a smear is prepared in a downstream unit (left side), the sample rack is transported along a front-located, linear "supply line" indicated by a left arrow so as to skip the measurement unit 41. Similarly to the transporting units 31 to 33, the transporting unit 34 is also provided with a measurement line and a supply line as shown in FIG. 1.

Based on the information read by the bar code unit, the transportation controller 6 determines a transportation destination for the sample located in the preprocessing unit 22, from among the measurement units 41. The transportation controller 6 controls the measurement line and the supply line of the transporting units 31 to 33 such that the sample is transported to the measurement unit 41 determined as the transportation destination. For example, when the transportation controller 6 has determined that the second-upstream measurement unit 41 as the transportation destination, the sample is transported along the supply line of the transporting unit 31 of the most-upstream measurement unit 41, and then transported to the measurement line of the transporting unit 32 of the second-upstream measurement unit 41.

Further, when a smear is needed to be prepared for the sample measured in the second upstream measurement unit 41, the sample is transported along the supply line of the transporting unit 33 located to the front of the most-downstream measurement unit 41, in accordance with the control by the transportation controller 6, and then transported to the measurement line of the transporting unit 34 for the smear preparing apparatus 5.

Each measurement line includes a linear area located at the most rear side and extending in the left-right direction, a right vessel area continuous to a right portion of the linear area, and a left vessel area continuous to a left portion of the linear area. A sample rack transported from the supply line into the right vessel area is then transported from the right vessel area to the right portion of the linear area, and then sent toward the left in the linear area, and the measurement for the sample is performed. Thereafter, the sample rack is sent to the left portion of the linear area, and then sent from the linear area to the left vessel area. Then, the sample rack is transported from the left vessel area to the supply line.

The three measurement units 41 extract sample containers from sample racks at predetermined positions (indicated by dotted arrows in FIG. 1) on the measurement lines (linear areas) of the transporting units 31 to 33, which are arranged to the front of the three measurement units 41, respectively, and measure the samples contained in the sample containers, respectively. When the measurement is completed, each measurement unit 41 returns the sample container to its corresponding holder of the sample rack from which the sample container is extracted.

The information processing unit 42 includes a computer 420, and a display input unit 426 formed of a touch-sensitive display. The computer 420 of the information processing unit 42 is communicably connected to the three measurement units 41, and controls operations of the three measurement units 41. Further, the computer 420 of the information processing unit 42 is communicably connected to sample supplying sections 3b (see FIG. 3) which are rear parts of the respective transporting units 31 to 33, and controls operations of the sample supplying sections 3b. Each sample supplying section 3b is composed of the right vessel area and the linear area in the measurement line of each of the transporting units 31 to 33.

Figure 3:
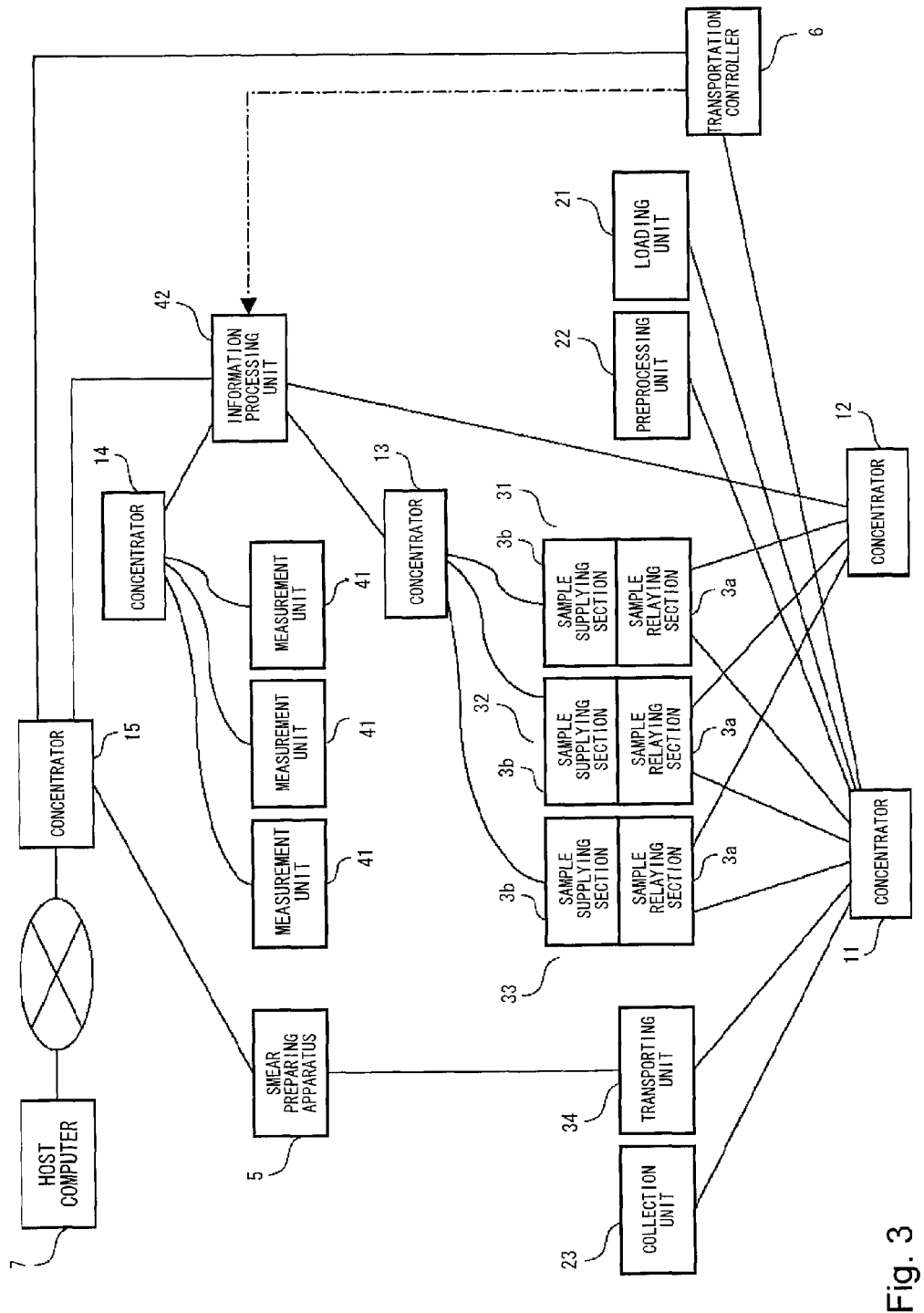
FIG. 3 schematically shows mutual connection relationship between units and apparatuses of a sample processing system according to an embodiment.

Further, an audio input terminal of the computer 420 of the information processing unit 42 is connected to an audio output terminal of a computer 600 of the transportation controller 6 by an analog signal cable for transmitting sound, as indicated by a long chain line in FIG. 3.

Further, the computer 420 of the information processing unit 42 is communicably connected to the host computer 7 through the communication network. The computer 420 of the information processing unit 42 inquires of the host computer 7 about a measurement order, and based on the result of the inquiry, issues measurement instructions to the measurement units 41, to cause the measurement units 41 to measure the sample. Each measurement unit 41 includes an optical detector for performing optical measurement of the sample, and the optical detector detects, as data of the sample, optical information (side fluorescence signal, forward scattered light signal, and side scattered light signal) from the blood cells in the measurement specimen. The computer 420 receives and analyzes the data of the sample from the measurement units 41, and transmits the result of the analysis such as a red blood cell count, a white blood cell count, and the like, to the host computer 7.

The smear preparing apparatus 5 is communicably connected to the host computer 7 through the communication network. The smear preparing apparatus 5 inquires of the host computer 7 about a measurement order, and based on the result of the inquiry, aspirates the sample contained in a sample container at a predetermined position (indicated by the dotted arrow in FIG. 1) on the measurement line of the transporting unit 34, and prepares a smear of the sample.

The collection unit 23 receives the sample rack transported by the transporting unit 34, and transports the received sample rack rearward, and accommodates it on a transportation path. The sample rack accommodated on the transportation path is taken out by the user, and the processing concerning the sample rack ends.

The transportation controller 6 is not provided with a display unit and an input unit, but is provided with only the computer 600. As shown in FIG. 3, the computer 600 is communicably connected to the host computer 7 through the communication network. The computer 600 of the transportation controller 6 controls transporting operations of the loading unit 21, the preprocessing unit 22, the collection unit 23, and sample relaying sections 3a (see FIG. 3), which are front parts of the respective transporting units 31 to 33, and the transporting unit 34. Each sample relaying section 3a is composed of the supply line and the left vessel area of the measurement line of each of the transporting units 31 to 33.

Figure 2:
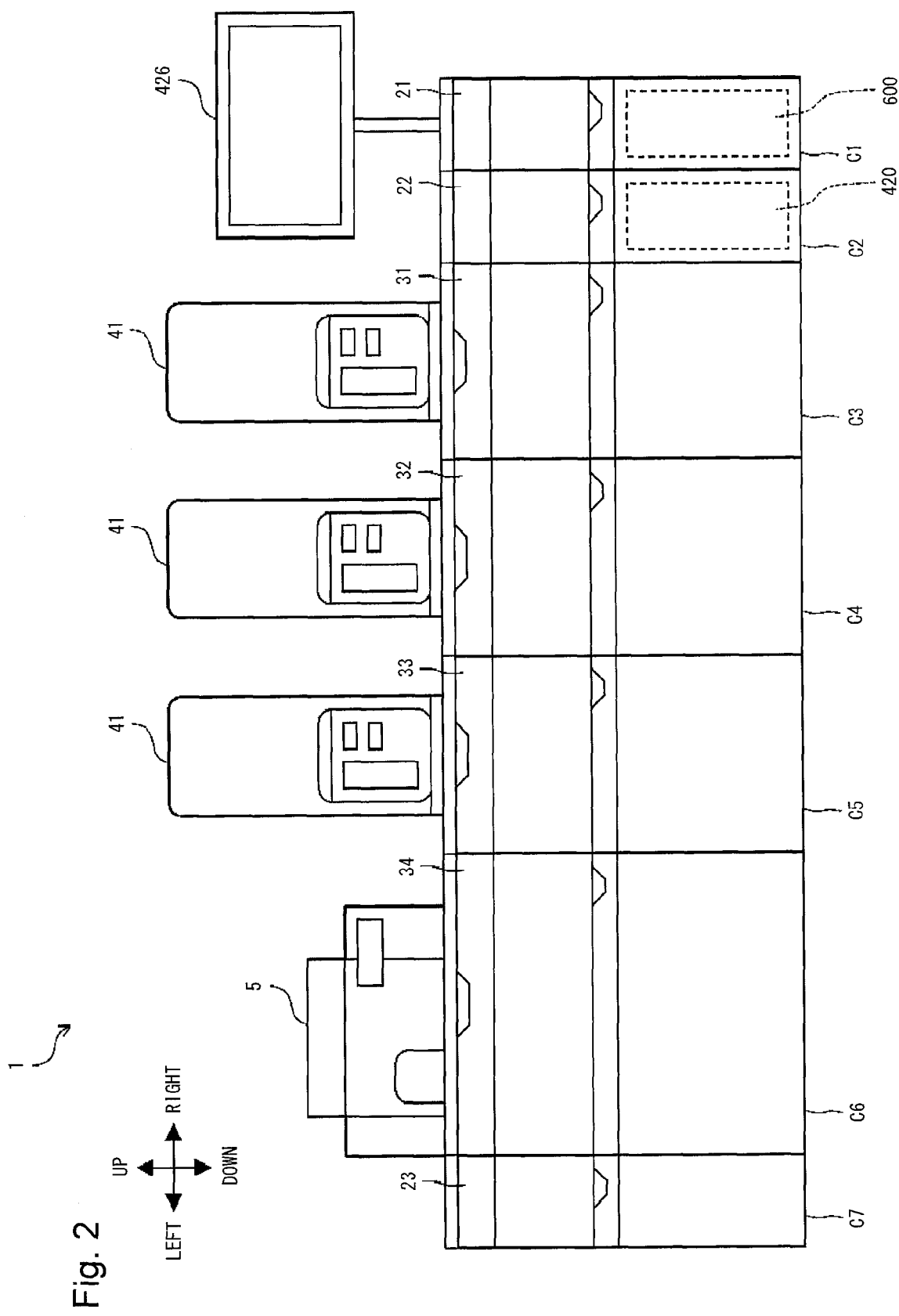
FIG. 2 schematically shows a configuration of a sample processing system according to an embodiment, viewed from the front thereof.

FIG. 2 schematically shows a configuration of the sample processing system 1, viewed from the front thereof.

As shown in FIG. 2, the loading unit 21, the preprocessing unit 22, the transporting units 31 to 34, and the collection unit 23 are installed in upper parts of wagons C1 to C7, respectively. That is, the wagons C1 to C7 support these units, respectively. In lower parts of the wagons C1 and C2, the computer 600 of the transportation controller 6 and the computer 420 of the information processing unit 42 are accommodated, respectively. The three measurement units 41, the smear preparing apparatus 5, the display input unit 426 of the information processing unit 42 are installed to the rear of the wagons C1 to C7.

FIG. 3 schematically shows mutual connection relationship between the units and apparatuses of the sample processing system 1.

Here, each of the transporting units 31 to 33 is shown, divided into the sample relaying section 3a and the sample supplying section 3b. As described above, each sample relaying section 3a is composed of the supply line and the left vessel area of the measurement line of each of the transporting units 31 to 33, and each sample supplying section 3b is composed of the right vessel area and the linear area of the measurement line of each of the transporting units 31 to 33.

The loading unit 21, the preprocessing unit 22, the collection unit 23, the three sample relaying sections 3a, the transporting unit 34, and the transportation controller 6 are communicably connected to a concentrator 11. The three sample relaying sections 3a and the information processing unit 42 are communicably connected to a concentrator 12. The three sample supplying sections 3b and the information processing unit 42 are communicably connected to a concentrator 13. The three measurement units 41 and the information processing unit 42 are communicably connected to a concentrator 14. The information processing unit 42, the transportation controller 6, the smear preparing apparatus 5, and the host computer 7, which is connected through the communication network, are communicably connected to a concentrator 15. Further, an analog audio signal outputted from the transportation controller 6 is inputted to the information processing unit 42, as indicated by a long chain line in FIG. 3.

Figure 4:
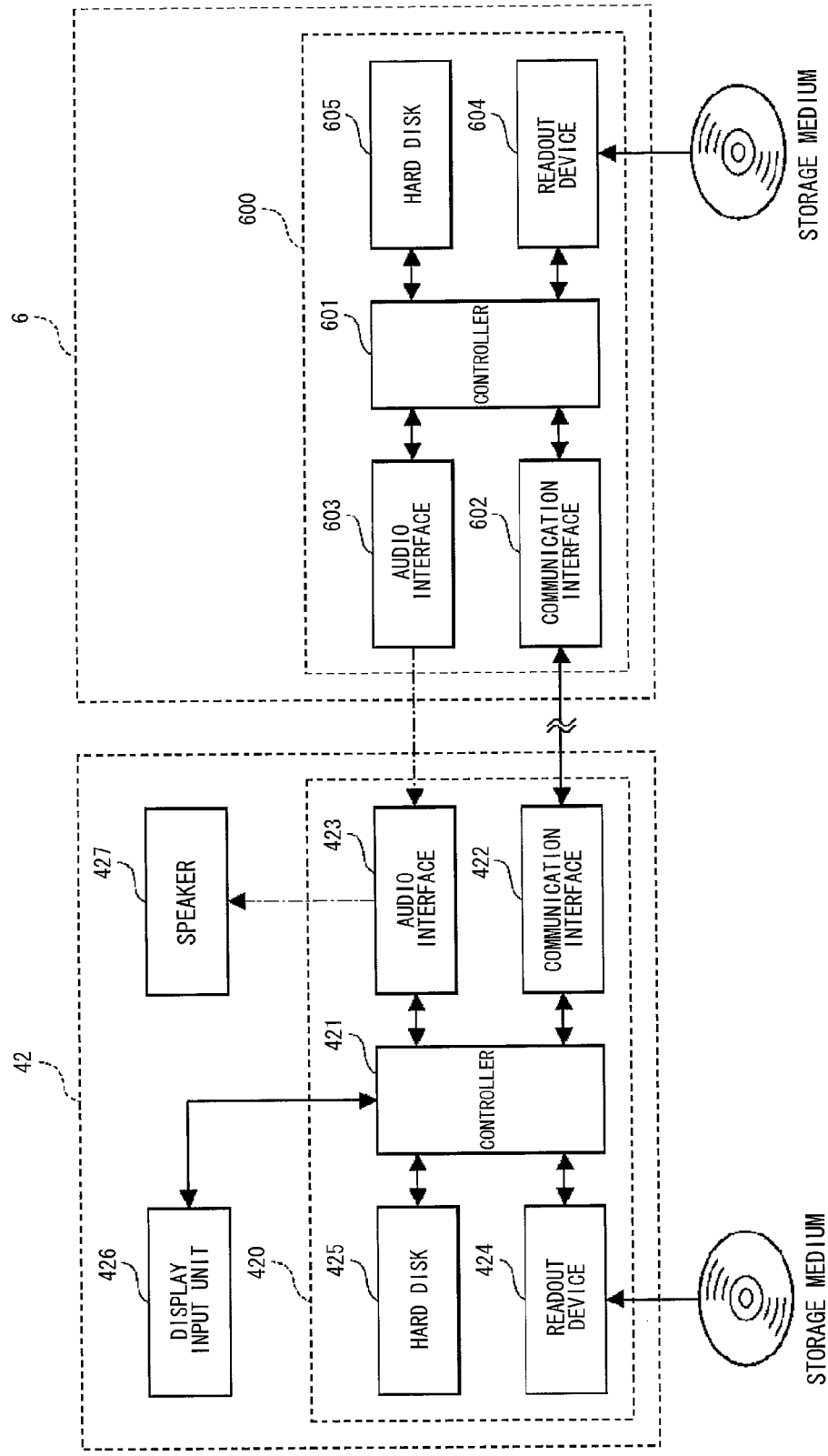
FIG. 4 shows circuit configurations of an information processing unit and a transportation controller according to an embodiment.

FIG. 4 shows circuit configurations of the information processing unit 42 and the transportation controller 6.

The information processing unit 42 includes the computer 420, the display input unit 426, and a speaker 427. The computer 420 includes a controller 421, a communication interface 422, an audio interface 423, a readout device 424, and a hard disk 425.

The controller 421 includes a CPU, a ROM, a RAM, and the like, and controls the components in the information processing unit 42 by executing a computer program stored in the hard disk 425. Moreover, signals outputted from the components of the information processing unit 42 are inputted to the controller 421.

The communication interface 422 transmits data inputted from the controller 421 to an external apparatus, and outputs data inputted from an external apparatus to the controller 421. Further, the communication interface 422 is connected to the units and apparatuses shown in FIG. 3. Accordingly, the computer 420 of the information processing unit 42 is communicably connected to the computer 600 of the transportation controller 6.

The audio interface 423 includes an audio output terminal and an audio input terminal. The audio interface 423 converts an audio signal (digital) inputted from the controller 421 and outputs an audio signal (analog) from the audio output terminal, and converts an audio signal (analog) inputted from the audio input terminal and outputs an audio signal (digital) to the controller 421. The audio output terminal of the audio interface 423 is connected to the speaker 427 via an analog signal cable, and the audio input terminal of the audio interface 423 is connected to the transportation controller 6 via an analog signal cable.

The readout device 424 is implemented as a CD drive, a DVD drive, or the like, and can read a computer program and data stored on a storage medium.

An operating system "Windows (registered trademark)" of Microsoft Corporation, a "remote desktop" application which is a communication application executable on Windows (registered trademark), and various computer programs and the like executable in the controller 421 are stored in the hard disk 425. Further, in the hard disk 425, there stored is a computer program for displaying a menu screen A1 (see FIGS. 5 to 7), a setting screen A100 (see FIG. 10A), and screens that are provided in a plurality of classes for the computer 420 of the information processing unit 42 and that are sequentially followed from the menu screen A1. The menu screen A1 and the screens for the computer 420 that are sequentially followed from the menu screen A1 are screens for displaying information of a measurement unit 41 controlled by the computer 420. From these screens, the user can operate the measurement unit 41.

The display input unit 426 is formed of a touch-sensitive display. The display input unit 426 displays an image based on a video signal outputted from the controller 421, and when the screen of the display input unit 426 is touched (pressed) by the user, the display input unit 426 outputs the inputted content to the controller 421. The speaker 427 outputs an audio signal (analog) inputted from the audio interface 423, as a sound.

The transportation controller 6 includes the computer 600. The computer 600 includes a controller 601, a communication interface 602, an audio interface 603, a readout device 604, and a hard disk 605. Since the transportation controller 6 is substantially the same as the information processing unit 42 from which the display input unit 426 and the speaker 427 are omitted, description of the communication interface 602 and the readout device 604 will be omitted.

The controller 601 includes a CPU, a ROM, a RAM and the like, and controls the transportation system by executing a computer program stored in the hard disk 605. Moreover, signals outputted from the components in the transportation system are inputted to the controller 601.

The audio output terminal of the audio interface 603 is connected to the information processing unit 42 via an analog signal cable, and the audio input terminal of the audio interface 603 is not used.

Similarly to the hard disk 425, an operating system "Windows (registered trademark)" of Microsoft Corporation, the "remote desktop" application, and various computer program and the like to be executed by the controller 601 are stored in the hard disk 605. Further, in the hard disk 605, there stored is a computer program for displaying a menu screen B1 (see FIG. 8), a setting screen B100 (see FIG. 10B), and screens that are provided in a plurality of classes for the computer 600 of the transportation controller 6 and that are sequentially followed from the menu screen B1. The menu screen B1 and the screens for the computer 600 that are sequentially followed from the menu screen B1 are screens for displaying information of the entire sample processing system 1. Through these screens, the user can confirm, for example, in which unit of the sample processing system 1 an abnormality has occurred, a state of measurement progress of a sample in a sample rack placed in the loading unit 21, and the like.

Figure 5:
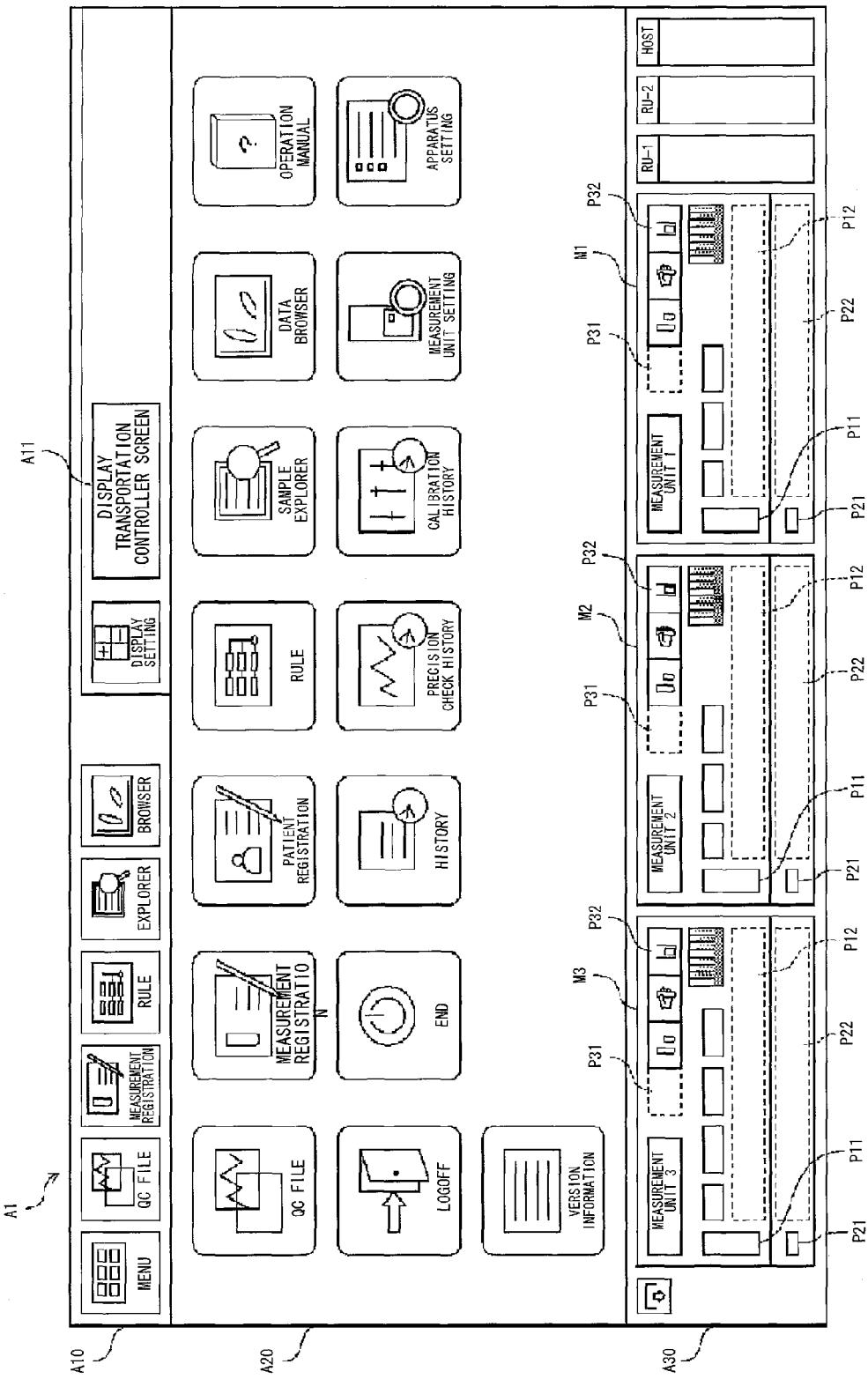
FIG. 5 shows a menu screen for a computer of an information processing unit displayed on a display input unit according to an embodiment.

FIG. 5 shows the menu screen A1 for the computer 420 of the information processing unit 42, displayed on the display input unit 426.

The menu screen A1 includes a toolbar area A10, a main area A20, and a measurement operation area A30.

The toolbar area A10 includes a screen switching button A11 and other buttons. Even when the display contents of the menu screen A1 are changed, or even when the menu screen A1 is switched to a screen of another class for the computer 420, the toolbar area A10 is always displayed in an upper part of the screen. The screen switching button A11 is displayed at a predetermined position in the toolbar area A10. Accordingly, the screen switching button A11 is always displayed on the same position on the display input unit 426 no matter how the screen for the computer 420 is changed.

When the screen switching button A11 is touched by the user, the menu screen B1 (see FIG. 8) for the computer 600 of the transportation controller 6 is displayed on the display input unit 426, instead of the menu screen A1.

The main area A20 includes a plurality of buttons for displaying various menus. The user can give various instructions to the computer 420 of the information processing unit 42 by touching these buttons.

It should be noted that, when a button other than the screen switching button A11 in the toolbar area A10 or a button in the main area A20 is touched, a screen of a class for the computer 420 other than the menu screen A1, is displayed on the display input unit 426. For example, when an "explorer" button in the toolbar area A10 or a "sample explorer" button in the main area A20 is touched, a screen listing measurement results is displayed. Also in this case, as described above, the screen switching button A11 is always displayed at the same position on the display input unit 426.

The measurement operation area A30 includes operation parts M1 to M3 respectively corresponding to the three measurement units 41. The operation parts M1 to M3 correspond to the right, center, left measurement units 41 shown in FIG. 1, respectively. Each of the operation parts M1 to M3 has a similar configuration, and includes status notification parts P11 and P21, error message display areas P12 and P22, and buttons P31 and P32.

Each status notification part P11 is displayed in green when its corresponding measurement unit 41 is operating normally, and is displayed in red when an error has occurred in the measurement unit 41. An error message is displayed in the error message display area P12 when an error has occurred in the measurement unit 41. The status notification part P21 is displayed in green when the sample supplying section 3b located to the front of the measurement unit 41 is operating normally, and is displayed in red when an error has occurred in the sample supplying section 3b. An error message is displayed in the error message display area P22 when an error has occurred in the sample supplying section 3b. In FIG. 5, since no error has occurred, the status notification parts P11 and P21 are displayed in green, and no error message is displayed in the error message display areas P12 and P22.

It should be noted that, when the status notification part P11 or P21 of any of the operation parts M1 to M3 is displayed in red upon occurrence of an error, an alarm sound is outputted from the speaker 427 of the information processing unit 42.

Each button P31 is a button for opening an error-handling screen D1 (see FIG. 6) used for handling an error, and is displayed when an error has occurred in its corresponding measurement unit 41. In FIG. 5, since no error has occurred in any of the measurement units 41, no button P31 is displayed. Each button P32 is a button for opening an operation part menu screen (not shown) capable of designating various processes.

Figure 6:
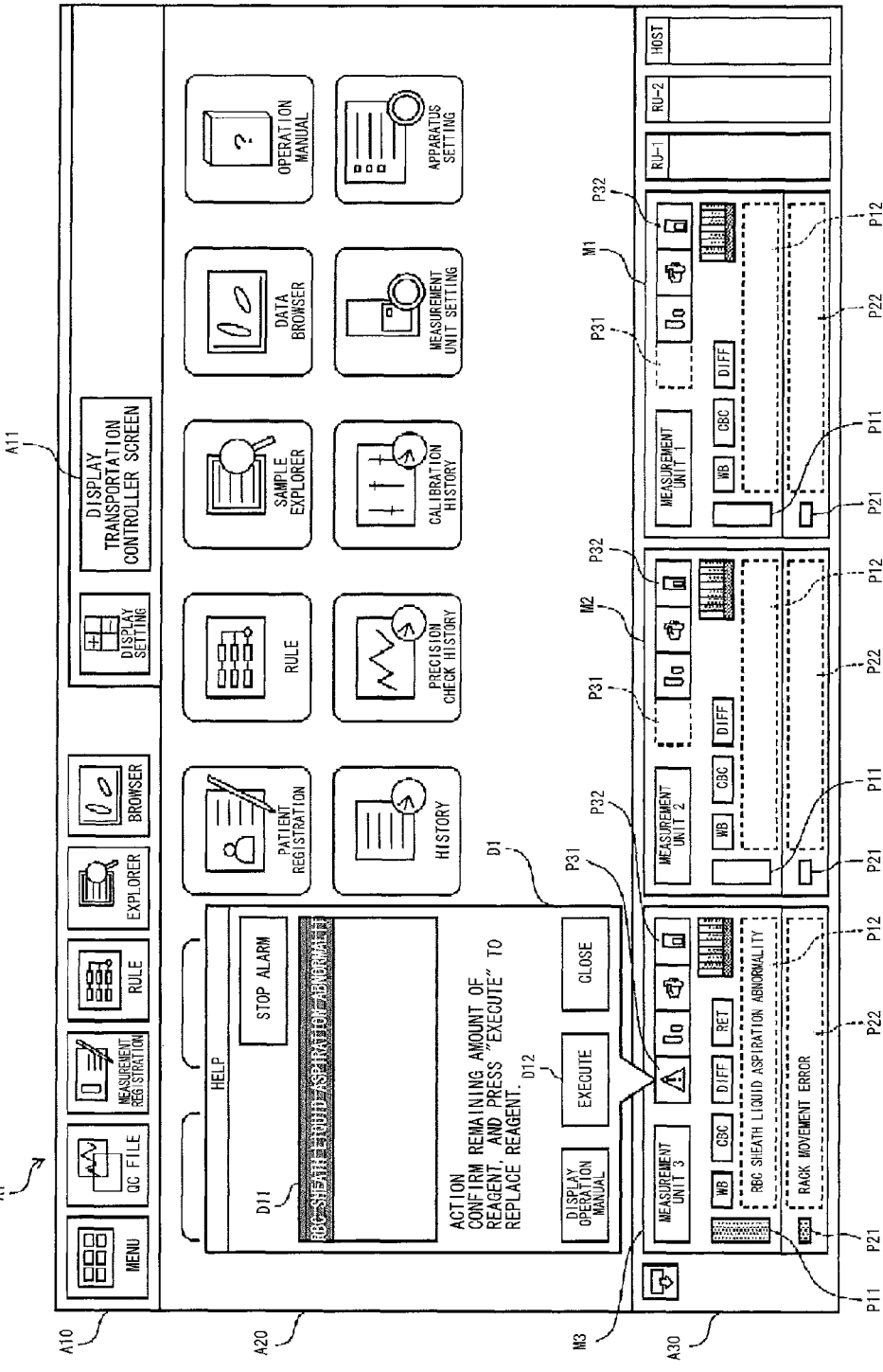
FIG. 6 shows a menu screen for an information processing unit in a state where an error-handling screen according to an embodiment is open.

FIG. 6 shows the menu screen A1 in a state where the error-handling screen D1 is open. FIG. 6 shows a state where an "RBC sheath liquid aspiration abnormality" has occurred in the left measurement unit 41 and a "rack movement error" has occurred in the left sample supplying section 3b.

In the operation part M3, the status notification parts P11 and P21 have turned into red due to the occurrence of the errors in the left measurement unit 41 and the sample supplying section 3b, respectively. Moreover, error messages are displayed in the error message display areas P12 and P22, respectively. Moreover, the button P31 containing an icon indicating an error alarm is displayed due to the occurrence of the error in the left measurement unit 41.

Here, when the button P31 is touched by the user while the button P31 is being displayed, the error-handling screen D1 is displayed, as shown in FIG. 6, above the operation part M3 which includes the button P31. The user can handle the error occurring in the left measurement unit 41, by inputting an instruction to the information processing unit 42 via the error-handling screen D1.

The error-handling screen D1 includes an error message list D11 and a button D12. In the error message list D11, an error content is displayed, and when a plurality of errors have simultaneously occurred, a plurality of error contents are displayed. Moreover, as shown in FIG. 6, in a case where an error has occurred due to a shortage of a reagent, when the button D12 is touched by the user, a reagent replacement screen D2 (see FIG. 7) for replacing the reagent for the measurement unit 41 (the left measurement unit 41 in this case) which caused the error is displayed.

Also when an error has occurred in either the right or the center measurement units 41, the user touches the button P31 displayed in the operation part M1 or M2 to cause the error-handling screen D1 to be displayed above the operation part M1 or M2, and thus can handle the error via the error-handling screen D1.

Figure 7:
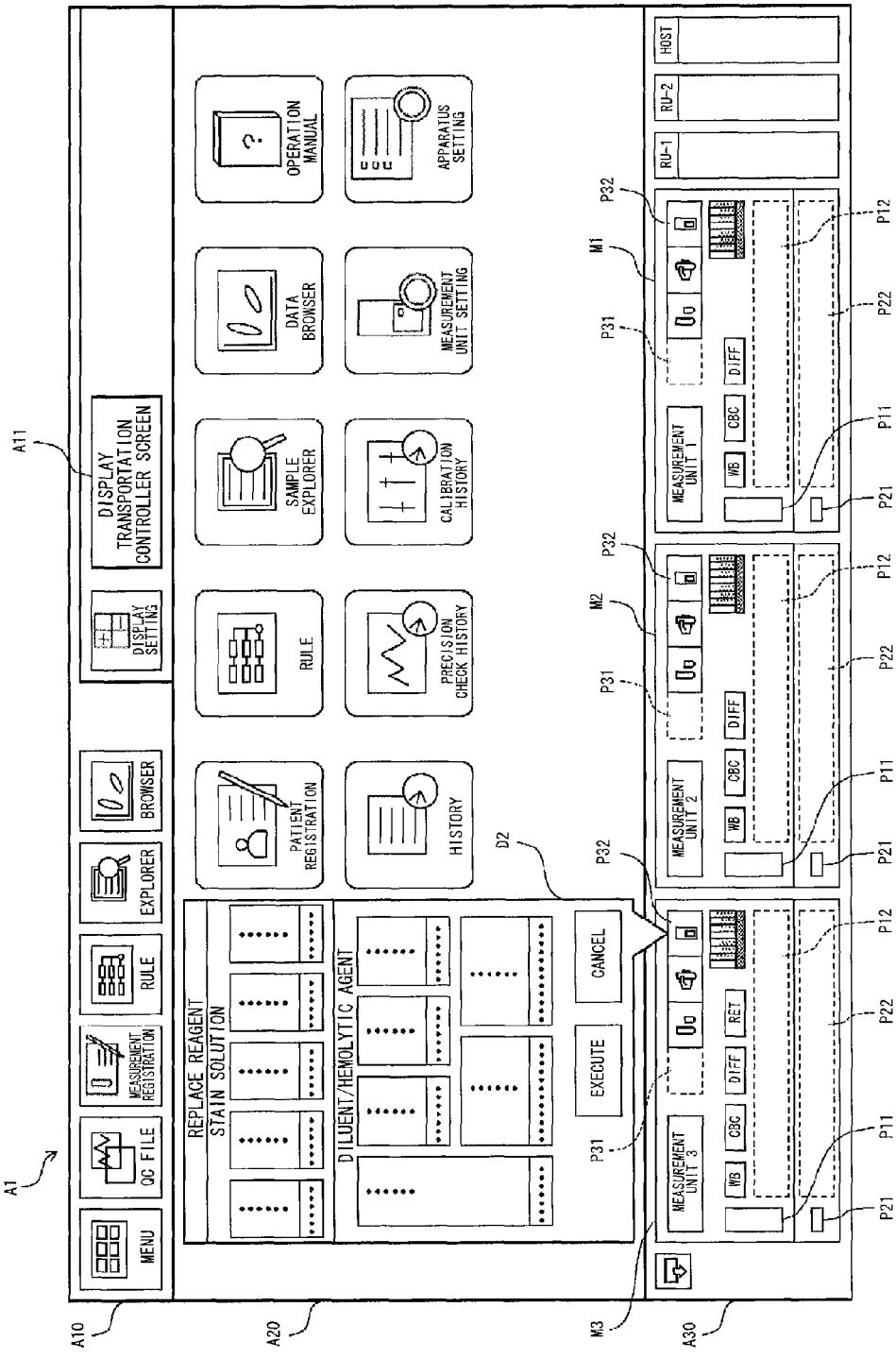
FIG. 7 shows a menu screen for an information processing unit in a state where a reagent replacement screen according to an embodiment is open.

FIG. 7 shows the menu screen A1 in a state where the reagent replacement screen D2 is open.

When the button P32 of any of the operation parts M1 to M3 is touched by the user, an operation part menu screen (not shown) capable of designating various processes is displayed above the operation part. When the user inputs an instruction to replace a reagent via the operation part menu screen, the reagent replacement screen D2 is displayed instead of the operation part menu screen. FIG. 7 shows a state where the reagent replacement screen D2 for replacing a reagent of the left measurement unit 41 is displayed. Eleven areas showing the states of eleven types of reagents used in the measurement unit 41 are set in the reagent replacement screen D2.

It should be noted that, as described above, also in the case where the button D12 of the error-handling screen D1 is touched while the error-handling screen D1 based on a shortage of a reagent is being displayed, the reagent replacement screen D2 is displayed.

Figure 8:
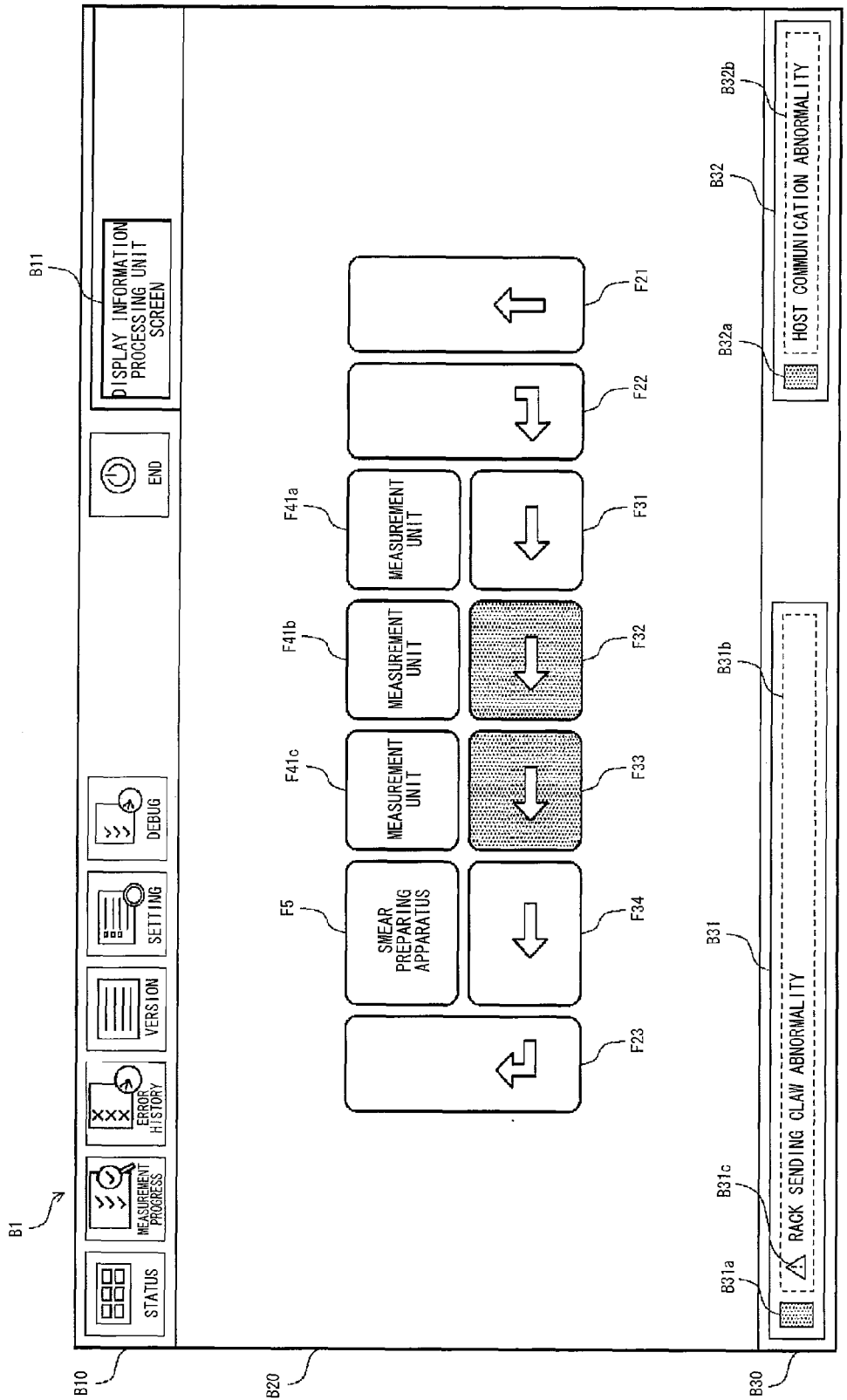
FIG. 8 shows a menu screen for a computer of a transportation controller displayed on a display input unit according to an embodiment.

FIG. 8 shows the menu screen B1 for the computer 600 of the transportation controller 6, displayed on the display input unit 426. This screen is displayed when the screen switching button A11 (see FIG. 5) is pressed.

The menu screen B1 includes a toolbar area B10, a layout area B20 and a state display area B30.

The toolbar area B10 includes a screen switching button B11 and other buttons. Even when the display contents of the menu screen B1 are changed, or even when the menu screen B1 is switched to a screen of another class for the computer 600, the toolbar area B10 is always displayed in an upper part of the screen. The screen switching button B11 is displayed at a predetermined position in the toolbar area B10. Accordingly, the screen switching button B11 is always displayed at the same position on the display input unit 426 no matter how the screen for the computer 600 is changed.

When the screen switching button B11 is touched by the user, a screen for the computer 420 of the information processing unit 42 (such as the menu screen A1) is displayed on the display input unit 426, instead of the menu screen B1.

It should be noted that, when a button other than the screen switching button B11 in the toolbar area B10 is touched, a screen of a class for the computer 600 of the transportation controller 6 other than the menu screen B1, is displayed on the display input unit 426. For example, when an "error history" button in the toolbar area B10 is touched, a screen showing a below-described history of errors detected by the computer 600 of the transportation controller 6 is displayed. Also in this case, as described above, the screen switching button B11 is always displayed at the same position on the display input unit 426.

In the layout area B20, an arrangement layout of the units and apparatuses of the sample processing system 1 is displayed. The layout area B20 includes display areas F21 to F23, F31 to F34, F41a to F41c, and F5, which respectively correspond to the loading unit 21, the preprocessing unit 22, the collection unit 23, the transporting units 31 to 34, the three measurement units 41, and the smear preparing apparatus 5. When an error has occurred in any of these units and apparatuses, its corresponding display area turns into red. The layout area B20 in FIG. 8 shows a state where errors have occurred in the transporting units 32 and 33.

The state display area B30 includes an internal state display area B31 and an external state display area B32. The internal state display area B31 indicates the state of the units and apparatuses shown in the layout area B20, and the external state display area B32 indicates the state of the host computer 7.

The internal state display area B31 includes a status notification part B31a and an error message display area B31b. When all of the units and apparatuses shown in the layout area B20 are operating normally, the status notification part B31a is displayed in green, and when an error has occurred in one or more units and apparatuses, the status notification part B31a is displayed in red. The type of the error that has occurred is displayed in the error message display area B31b. The internal state display area B31 in FIG. 8 shows that a "rack sending claw abnormality" has occurred in any of the units and apparatuses.

Moreover, when an error has occurred in any of the units and apparatuses shown in the layout area B20, an error alarm icon B31c is displayed at the left end of the error message display area B31b.

When the error alarm icon B31c is touched by the user, a screen similar to the error-handling screen D1 (see FIG. 6) is displayed on the menu screen B1. Through this screen, the user can understand in which unit or apparatus the error has occurred, and thus, can handle the error.

The external state display area B32 includes a status notification part B32a and an error message display area B32b. The status notification part B32a is displayed in green when the host computer 7 is operating normally, and is displayed in red when an error has occurred in the host computer 7 and when an error has occurred in the communication with the host computer 7. The type of the error that has occurred is displayed in the error message display area B32b. The external state display area B32 in FIG. 8 shows that a "host communication abnormality" indicating that the computer 600 of the transportation controller 6 cannot communicate with the host computer 7.

It should be noted that, when the status notification part B31a or B32a is displayed in red due to an occurrence of an error, an audio signal for outputting an alarm sound is outputted from the audio interface 603 of the transportation controller 6, and this audio signal is inputted to the audio interface 423 of the information processing unit 42.

Figure 9A:
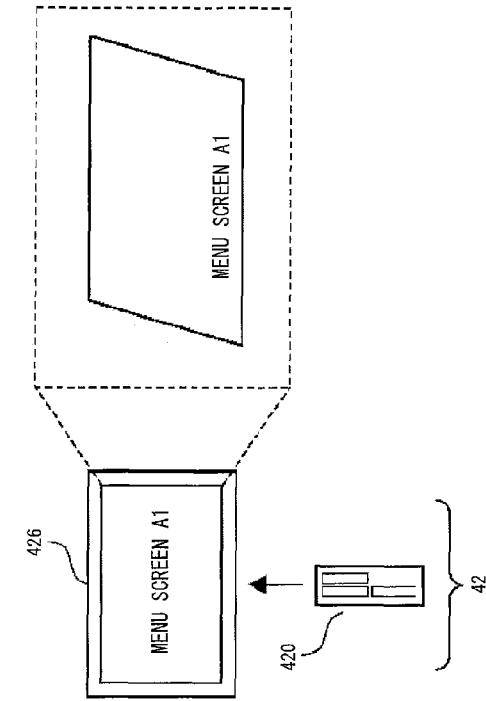
FIG. 9A and FIG. 9B are diagrams for describing switching of screens on a display input unit according to an embodiment.
Figure 9B:
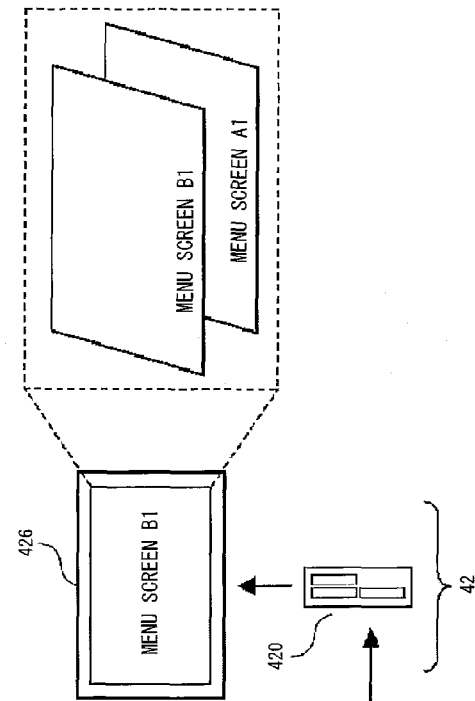

FIG. 9 is a diagram for describing switching of screens on the display input unit 426. With reference to FIG. 9A and FIG. 9B, the menu screen A1 for the computer 420 of the information processing unit 42 is displayed on the display input unit 426, and the menu screen B1 for the computer 600 of the transportation controller 6 is displayed on the display input unit 426.

With reference to FIG. 9A, a video signal outputted from the computer 420 of the information processing unit 42 contains the menu screen A1. The computer 600 of the transportation controller 6 is configured to be able to output a video signal containing the menu screen B1 that is to be displayed at the frontmost of the screens. However, in the present embodiment, no display unit for displaying a video signal is connected the computer 600. Accordingly, only the menu screen A1 for the computer 420 of the information processing unit 42 is displayed on the display input unit 426.

With reference to FIG. 9B, when the screen switching button A11 of the menu screen A1 is touched in the state shown in FIG. 9A, the computer 420 of the information processing unit 42 starts communication with the computer 600 of the transportation controller 6 using the remote desktop application. At this time, the computer 420 of the information processing unit 42 communicates with the computer 600 of the transportation controller 6 using the remote desktop application, and displays the menu screen B1 on top of the menu screen A1 as shown in FIG. 9B. As a result, only the menu screen B1 is displayed on the display input unit 426, instead of the menu screen A1.

When the communication using the remote desktop application is established, the user who has been logging on the transportation controller 6 is logged off. Moreover, an audio signal (digital) outputted from the controller 601 of the transportation controller 6 to the audio interface 603 is further transmitted from the communication interface 602 to the information processing unit 42 through the communication using the remote desktop application.

Figure 10A:
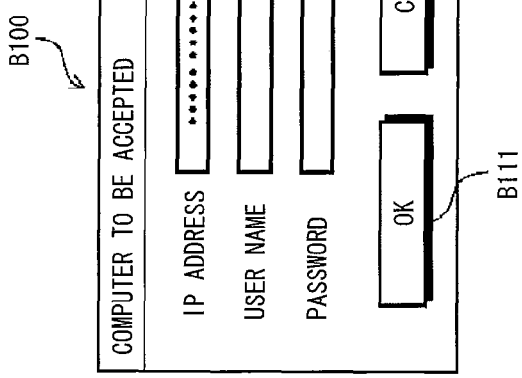
FIG. 10A and FIG. 10B show setting screens for setting a remote desktop application in an information processing unit and a transportation controller according to an embodiment, respectively.

FIG. 10A shows the setting screen A100 for setting the remote desktop application in the information processing unit 42.

The setting screen A100 includes text boxes A101 to A103, an OK button A111, and a cancel button A112. The text boxes A101 to A103 are areas for accepting an IP address of the computer 600 of the transportation controller 6, which is a connection destination for the remote desktop application, a user name for logging on the computer 600 of the transportation controller 6, and a password corresponding to the user name, respectively. When the OK button A111 is touched, the settings of the remote desktop application containing the contents of the text boxes A101 to A103 are stored in the hard disk 425 of the information processing unit 42. When the cancel button A112 is touched, the contents of the text boxes A101 to A103 are deleted, and the setting screen A100 is closed.

Here, the settings of the remote desktop application in the information processing unit 42 are set by a service person when the sample processing system 1 is to be installed in the laboratory. First, the service person logs on using his or her user name from a start-up screen of the information processing unit 42. After the service person has logged on using his or her name, a menu button (not shown) for the service person appears in the menu screen A1 displayed next. By operating this menu button, the service person causes the setting screen A100 to be displayed on the display input unit 426. In this manner, the setting is performed by the service person via the setting screen A100.

Figure 10B:
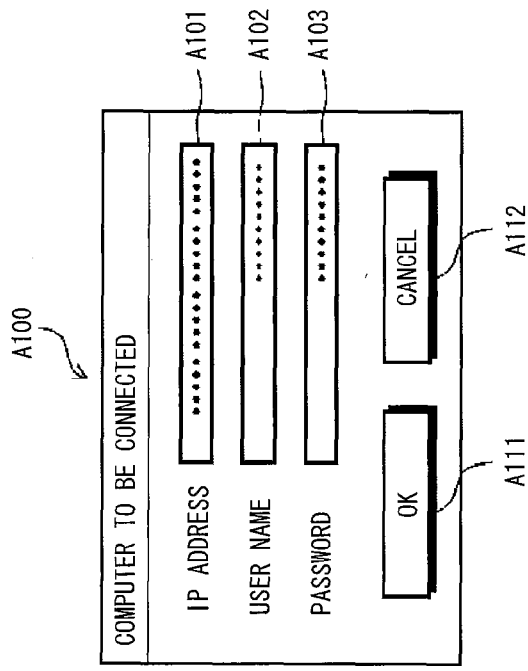

FIG. 10B shows the setting screen B100 for setting the remote desktop application in the transportation controller 6.

The setting screen B100 includes text boxes B101 to B103, an OK button B111, and a cancel button B112. The text boxes B101 to B103 are areas for accepting an IP address of the computer 420 of the information processing unit 42 which will connect to the computer 600 of the transportation controller 6 by use of the remote desktop application, a user name for logging on the computer 600 of the transportation controller 6, and a password corresponding to the user name, respectively. When the OK button B111 is touched, the settings of the remote desktop application containing the contents of the text boxes B101 to B103 are stored in the hard disk 605 of the transportation controller 6. When the cancel button B112 is touched, the contents of the text boxes B101 to B103 are deleted, and the setting screen B100 is closed.

Here, the settings of the remote desktop application in the transportation controller 6 are set by a service person when the sample processing system 1 is to be installed. First, the service person temporarily connects a display unit and an input unit to the transportation controller 6, and activates a computer program for setting the remote desktop application which is stored in the hard disk 605 in advance. When the computer program for setting the remote desktop application is activated, a menu screen (not shown) for performing various settings is displayed on the display unit, and the service person operates this menu screen to cause the setting screen B100 to be displayed on the display unit. In this manner, the setting is performed by the service person via the setting screen B100. It should be noted that the input unit used by the service person may be accommodated in the wagon C1 and connected to the transportation controller 6 in advance.

As described above, after the remote desktop application has been set via the setting screen A100 shown in FIG. 10A and the setting screen B100 shown in FIG. 10B, the screen switching button A11 is displayed on the menu screen A1, and the screen switching button B11 is displayed on the menu screen B1. Then, when the screen switching button A11 is touched on the menu screen A1, a logon process is performed onto the computer 600 of the transportation controller 6, and the menu screen B1 is displayed on the display input unit 426. When the screen switching button B11 is touched on the menu screen B1, a logoff process is performed onto the computer 600 of the transportation controller 6, and the menu screen A1 is displayed on the display input unit 426. It should be noted that, as described above, the screen switching buttons A11 and B11 are displayed in the same manner, also on screens for the computer 420 of the information processing unit 42 and screens for the computer 600 of the transportation controller 6, other than the menu screen A1 and B1.

Next, with reference to FIG. 11, description will be given of processes performed by the computer 420 of the information processing unit 42 and by the computer 600 of the transportation controller 6 when a screen displayed on the display input unit 426 of the information processing unit 42 is to be switched.

Figure 11A:
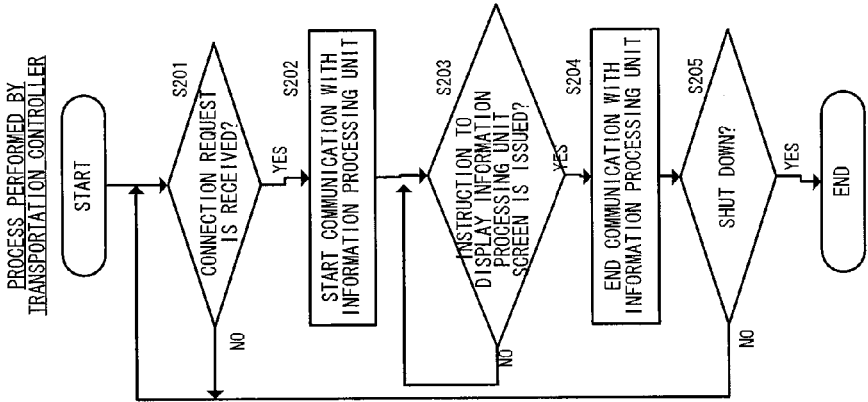
FIG. 11A and FIG. 11B are flow charts showing processes performed by a computer of an information processing unit and a computer of a transportation controller when screens are switched according to an embodiment, respectively.

FIG. 11A is a flow chart showing processes performed by the computer 420 of the information processing unit 42.

The controller 421 of the information processing unit 42 waits without performing a process until the controller 421 receives an instruction to display the menu screen B1 for the computer 600 of the transportation controller 6 while a screen for the computer 420 of the information processing unit 42 (such as the menu screen A1) is being displayed on the display input unit 426, that is, until the screen switching button A11 is touched by the user (S101).

When the screen switching button A11 is touched (S101: YES), the controller 421 transmits, based on the settings set in advance via the setting screen A100, a request to establish connection using the remote desktop application to the computer 600 of the transportation controller 6 via the communication interface 422 (S102). As a result, communication using the remote desktop application is started between the computer 420 of the information processing unit 42 and the computer 600 of the transportation controller 6 (S103), and the menu screen B1 is displayed on the display input unit 426, instead of the screen for the computer 420 of the information processing unit 42 (such as the menu screen A1).

Subsequently, the controller 421 waits without performing a process until the controller 421 receives an instruction to display a screen for the computer 420 of the information processing unit 42 (such as the menu screen A1) while a screen for the computer 600 of the transportation controller 6 (such as the menu screen B1) is being displayed on the display input unit 426, that is, until the screen switching button B11 is touched by the user (S104).

When the screen switching button B11 is touched (S104: YES), the controller 421 ends the communication using the remote desktop application with the computer 600 of the transportation controller 6 (S105). As a result, a screen for the computer 420 of the information processing unit 42 (such as the menu screen A1) is displayed on the display input unit 426. The controller 421 repeats the processes of S101 to S105 until a shut-down instruction to the information processing unit 42 (S106) is issued.

Figure 11B:
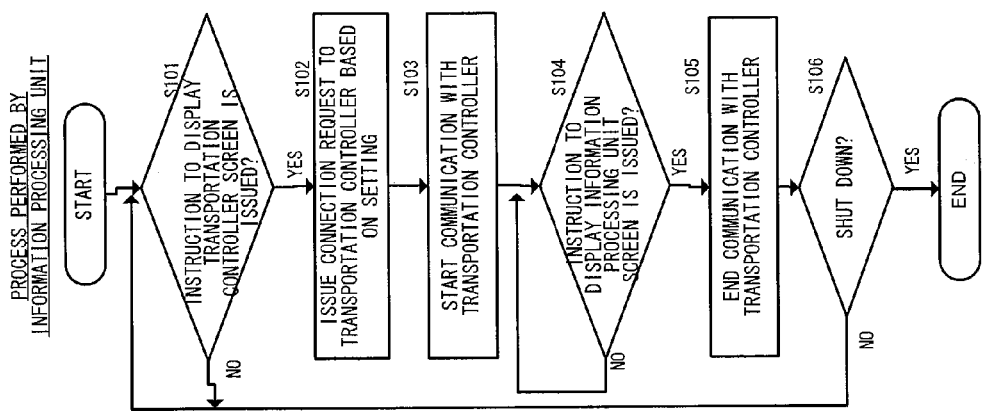

FIG. 11B is a flow chart showing processes performed by the computer 600 of the transportation controller 6.

The controller 601 of the transportation controller 6 waits without performing a process until the controller 601 receives, via the communication interface 602, the connection request transmitted from the computer 420 of the information processing unit 42 in S102 of FIG. 11A (S201). Upon receiving the connection request (S201: YES), the controller 601 permits the connection request from the computer 420 of the information processing unit 42, based on the settings set in advance via the setting screen B100. As a result, communication using the remote desktop application is started between the computer 420 of the information processing unit 42 and the computer 600 of the transportation controller 6 (S202). It should be noted that, when the user name and the password contained in the connection request are different from those set on the setting screen B100, the connection request is not permitted.

Subsequently, the controller 601 waits without performing a process until the screen switching button B11 is touched by the user through the communication using the remote desktop application (S203). When the screen switching button B11 is touched (S203: YES), the controller 601 ends the communication using the remote desktop application with the computer 420 of the information processing unit 42 (S204). The controller 601 repeats the processes of S201 to S204 until a shut-down instruction to the transportation controller 6 is issued (S205).

Figure 12C:
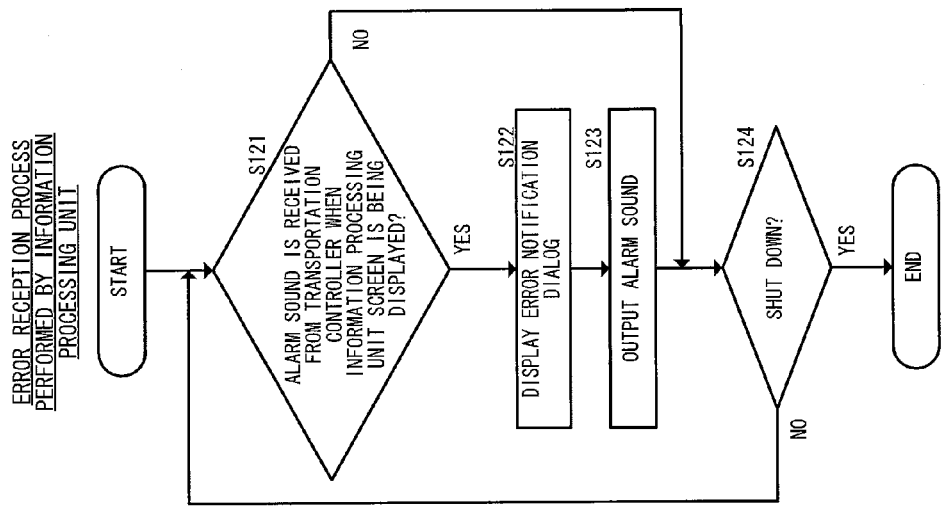
FIG. 12A, FIG. 12B, and FIG. 12C are flow charts showing processes performed by a computer of an information processing unit at an occurrence of an error, processes performed by a computer of a transportation controller at an occurrence of an error, and error reception processes performed by a computer of an information processing unit according to an embodiment, respectively.
Figure 12B:
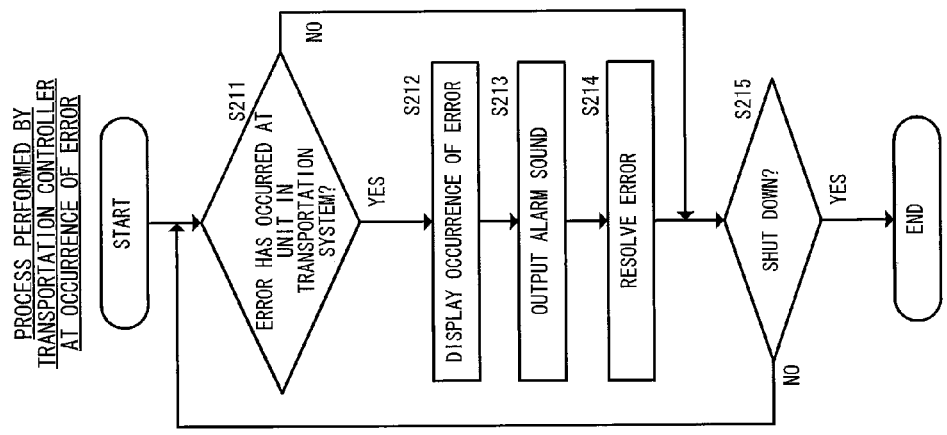
Figure 12A:
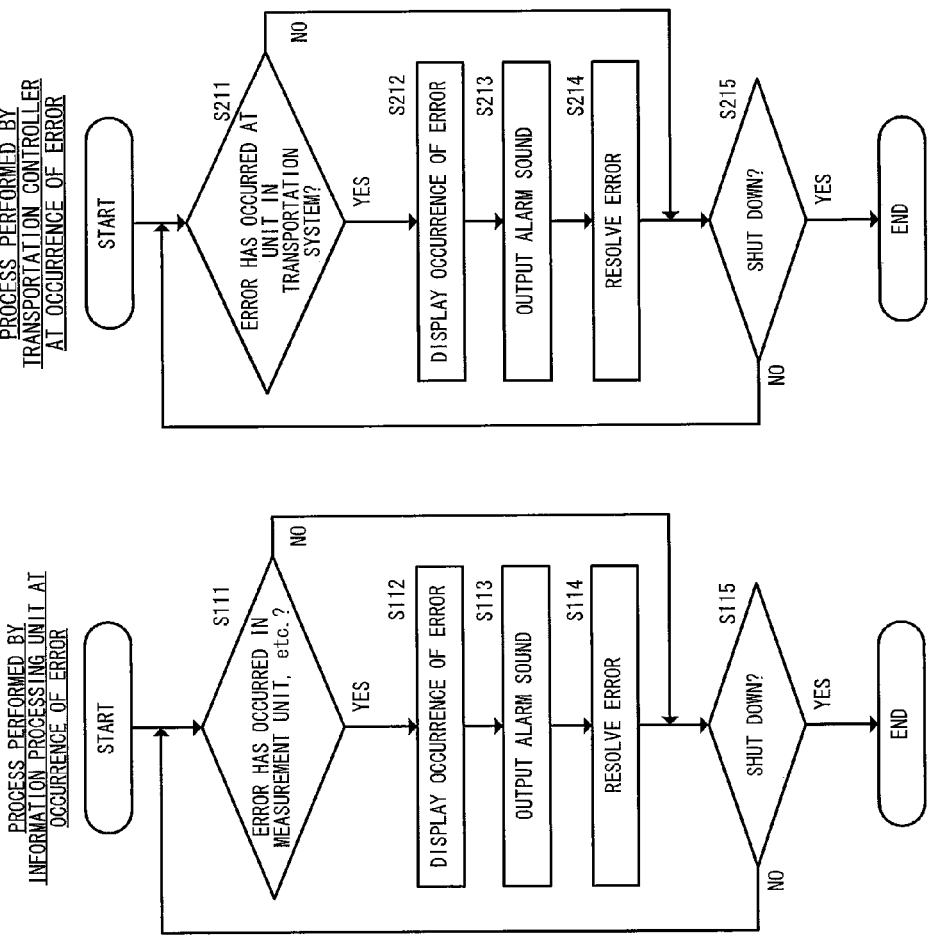

FIG. 12A is a flow chart showing processes performed by the computer 420 of the information processing unit 42, at an occurrence of an error. These processes are performed upon activation of the information processing unit 42.

The controller 421 of the information processing unit 42 is monitoring whether an error has occurred in any of the three measurement units 41 and the three sample supplying sections 3b (S111). Upon occurrence of an error in any of the units (S111: YES), the controller 421 causes, in accordance with the place where the error has occurred, the status notification part P11 or P21 to be displayed in red, an error message to be displayed in the error message display area P12 or P22, and the button P31 to be displayed, as shown in FIG. 6 (S112). Moreover, the controller 421 causes an alarm sound to be outputted from the speaker 427 (S113). Accordingly, when the computer 420 of the information processing unit 42 detects an error while a screen for the computer 420 of the information processing unit 42 is being displayed on the display input unit 426, the occurrence of the error is displayed as shown in FIG. 6 and an error is notified of by means of the alarm sound.

It should be noted that, also when the computer 420 of the information processing unit 42 has detected an error while a screen for the computer 600 of the transportation controller 6 is being displayed on the display input unit 426, the controller 421 causes an alarm sound to be outputted from the speaker 427. Accordingly, even when a screen for the computer 600 of the transportation controller 6 is being displayed on the display input unit 426, the user can know that the computer 420 of the information processing unit 42 has detected an error. In this case, a message indicating that the computer 420 of the information processing unit 42 has detected an error may be displayed on top of the screen for the computer 600 of the transportation controller 6. An error detected by the computer 420 of the information processing unit 42 may include, for example, a shortage of a reagent in a measurement unit 41, an abnormal operation by a sample aspirator, and the like.

When the user has handled and resolved the error (S114), the process is advanced to S115. The controller 421 repeats the processes of S111 to S114 until a shut-down instruction to the information processing unit 42 is issued (S114).

FIG. 12B is a flow chart showing processes performed by the computer 600 of the transportation controller 6, at an occurrence of an error. These processes are performed upon activation of the transportation controller 6.

The controller 601 of the transportation controller 6 is monitoring whether an error has occurred in any of the units and apparatuses shown in the layout area B20 in FIG. 8 (S211). When an error has occurred in any of the units and apparatuses (S211: YES), the controller 601 causes the occurrence of the error to be displayed in accordance with the place where the error has occurred, as shown in the example of FIG. 8 (S212). Moreover, the controller 601 causes an audio signal for outputting an alarm sound to be outputted from the audio output terminal of the audio interface 603 (S213). Further, in a case where communication using the remote desktop application is being performed with the computer 420 of the information processing unit 42, an audio signal (digital) for outputting an alarm sound is transmitted to the computer 420 of the information processing unit 42 through the communication using the remote desktop application, and is outputted from the speaker 427 of the information processing unit 42. As a result, when the computer 600 of the transportation controller 6 has detected an error while a screen for the computer 600 of the transportation controller 6 is being displayed on the display input unit 426, the occurrence of the error is displayed as shown in the example of FIG. 8 and the error is notified of by means of an alarm sound.

When the user has handled and resolved the error (S214), the process is advanced to S215. The controller 601 repeats the processes of S211 to S214 until a shut-down instruction to the transportation controller 6 is issued (S214).

FIG. 12C is a flow chart showing error reception processes performed by the computer 420 of the information processing unit 42. These processes are performed upon activation of the information processing unit 42.

The controller 421 of the information processing unit 42 is monitoring whether an alarm sound has been received from the transportation controller 6 via the audio interface 423, while a screen for the computer 420 of the information processing unit 42 (such as the menu screen A1) is being displayed (S121). Here, a computer program for monitoring a sound inputted to the audio input terminal of the audio interface 423 is stored in the hard disk 425 of the information processing unit 42. This computer program is executed upon activation of the information processing unit 42, and determines that an alarm sound has been received when an audio signal was inputted to the audio input terminal over a predetermined time period. This computer program may be configured to determine whether the inputted sound is an alarm sound, by analyzing the wave length, the cycle, and the like of the audio signal inputted to the audio input terminal. In this case, the alarm sound needs to have a unique pattern different from those of other sounds.

Figure 13:
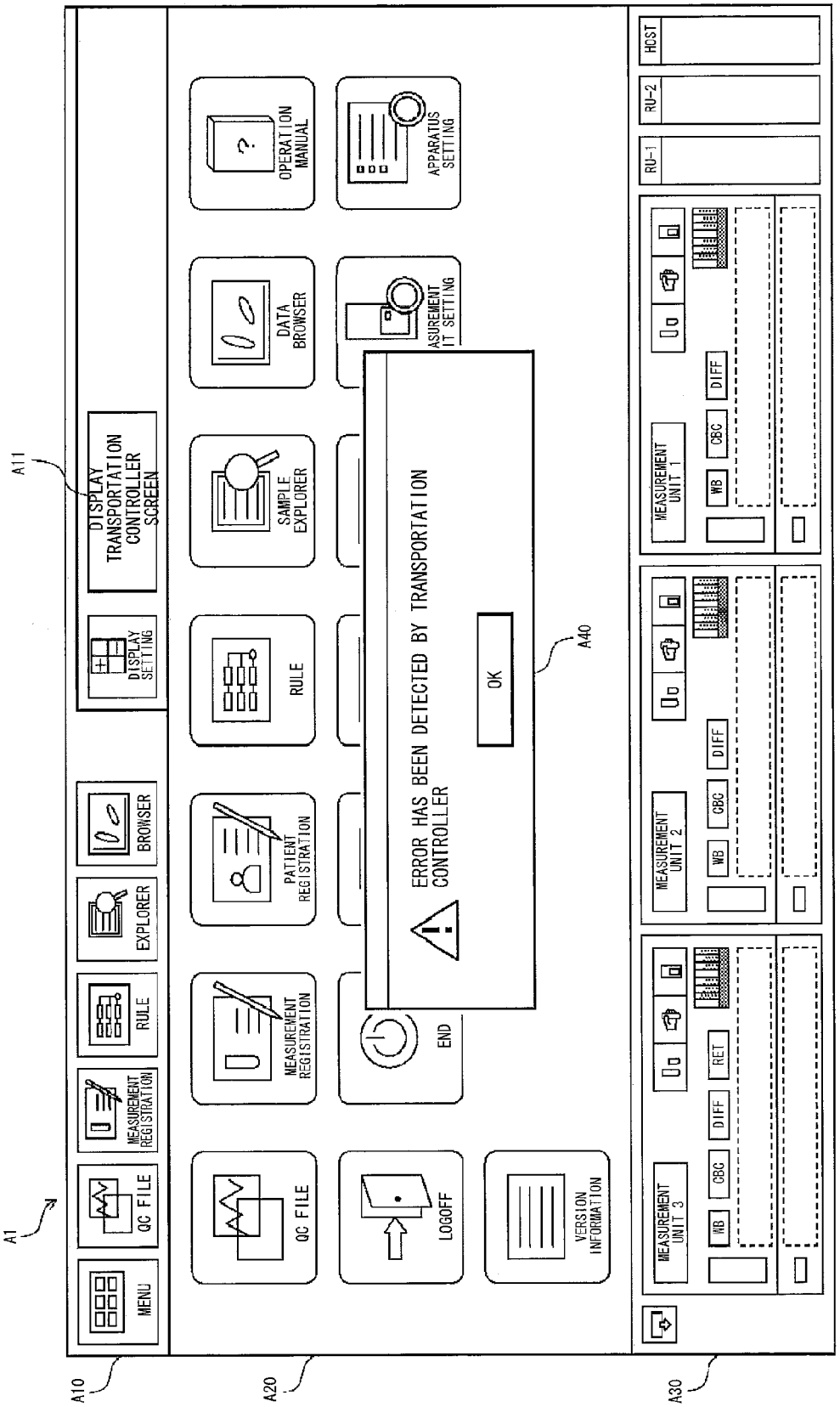
FIG. 13 shows an error notification dialog according to an embodiment.

Upon receiving the alarm sound from the transportation controller 6 (S121: YES), the controller 421 causes an error notification dialog A40 shown in FIG. 13 to be displayed on top of the screen for the computer 420 of the information processing unit 42 (S122), and causes the alarm sound to be outputted from the speaker 427 (S123). In FIG. 13, the error notification dialog A40 is displayed on top of the menu screen A1 for the computer 420 of the information processing unit 42. It should be noted that the message displayed in the error notification dialog A40 may be "Switch the screen to confirm the error". The controller 421 repeats the processes of S121 to S123 until a shut-down instruction to the information processing unit 42 is issued (S124).

As described above, according to the present embodiment, it is possible to cause a screen for the computer 420 of the information processing unit 42 (such as the menu screen A1) and a screen for the computer 600 of the transportation controller 6 (such as the menu screen B1) to be displayed on the single display input unit 426 which is connected to the information processing unit 42. Moreover, it is possible to operate these two screens via the single display input unit 426. Accordingly, it is not necessary to provide the transportation controller 6 with a display unit and an input unit (or a display input unit), and thus, it is possible to effectively utilize space in the laboratory.

Moreover, according to the present embodiment, since it is not necessary to provide the transportation controller 6 with a display unit and an input unit by means of which display and input is performed, it is possible to reduce costs for the sample processing system 1 and to reduce burden on the environment. Moreover, it is not necessary to separately provide hardware resources such as a changeover switch in order to switch the screen between a screen for the computer 420 of the information processing unit 42 (such as the menu screen A1) and a screen for the computer 600 of the transportation controller 6 (such as the menu screen B1). Therefore, it is possible to further reduce burden on the environment, compared with a case where the screens are switched by use of a changeover switch or the like.

Moreover, according to the present embodiment, the screen switching button A11 is always displayed at a predetermined position in a screen for the computer 420 of the information processing unit 42 (such as the menu screen A1), and the screen switching button B11 is always displayed at a predetermined position in a screen for the computer 600 of the transportation controller 6 (such as the menu screen B1). Accordingly, the user can easily switch the screens.

Moreover, according to the present embodiment, since the computer 420 of the information processing unit 42 and the computer 600 of the transportation controller 6 are accommodated in the wagon C1 and C2, respectively, wider space can be secured in the laboratory. Moreover, since the information processing unit 42 is provided with the touch-sensitive display input unit 426, an input device such as a keyboard need not be provided separately, and thus, wider space can be secured in the laboratory.

Moreover, according to the present embodiment, even when a screen for the computer 420 of the information processing unit 42 (such as the menu screen A1) is being displayed on the display input unit 426, the user can know that the computer 600 of the transportation controller 6 has detected an error through the error notification dialog A40 displayed on top of the screen and an alarm sound outputted from the speaker 427. Moreover, even when a screen for the computer 600 of the transportation controller 6 (such as the menu screen B1) is being displayed on the display input unit 426, the user can understand that the computer 420 of the information processing unit 42 has detected an error through an alarm sound outputted from the speaker 427.

An embodiment of the present invention has been described as above. However, the present invention is not limited to the above embodiment.

For example, in the example of the above embodiment, blood is used as a subject to be measured. However, urine may be used as a subject to be measured. That is, the present invention can be applied to a sample processing system that tests urine, and further, the present invention can be applied to clinical sample processing systems that test other clinical samples.

Further, in the above embodiment, in order to switch the menu screen A1 or the like displayed on the display input unit 426 to the menu screen B1 or the like, and vice versa, the screen switching buttons A11 and B11 are used. However, the present invention is not limited thereto. Instead of the screen switching buttons A11 and B11, a link to the screen to be displayed, which link is indicated by a character string, may be used. Further, an icon may be used instead of the link.

Further, in the above embodiment, the screen switching button A11 is provided in the menu screen A1, and the screen switching button B11 is provided in the menu screen B1. However, the present invention is not limited thereto. For example, while a menu screen is being displayed on the display input unit 426, a screen switching button may be displayed in a display area outside the frame of the menu screen.

Further, in the above embodiment, the information processing unit 42 controls the three measurement units 41. However, the present invention is not limited thereto. The information processing unit 42 may control the smear preparing apparatus 5 in addition to the three measurement units 41. Moreover, the target to be controlled by the information processing unit 42 may include not only the measurement units 41 which measure samples and the smear preparing apparatus 5 which prepares smears, but also an agitating unit which agitates a sample container, a dispensing unit which dispenses a sample, and the like.

Further, in the above embodiment, the three measurement units 41 are controlled by the single information processing unit 42. However, the three measurement units 41 may be controlled by two or more information processing units.

Figure 14:
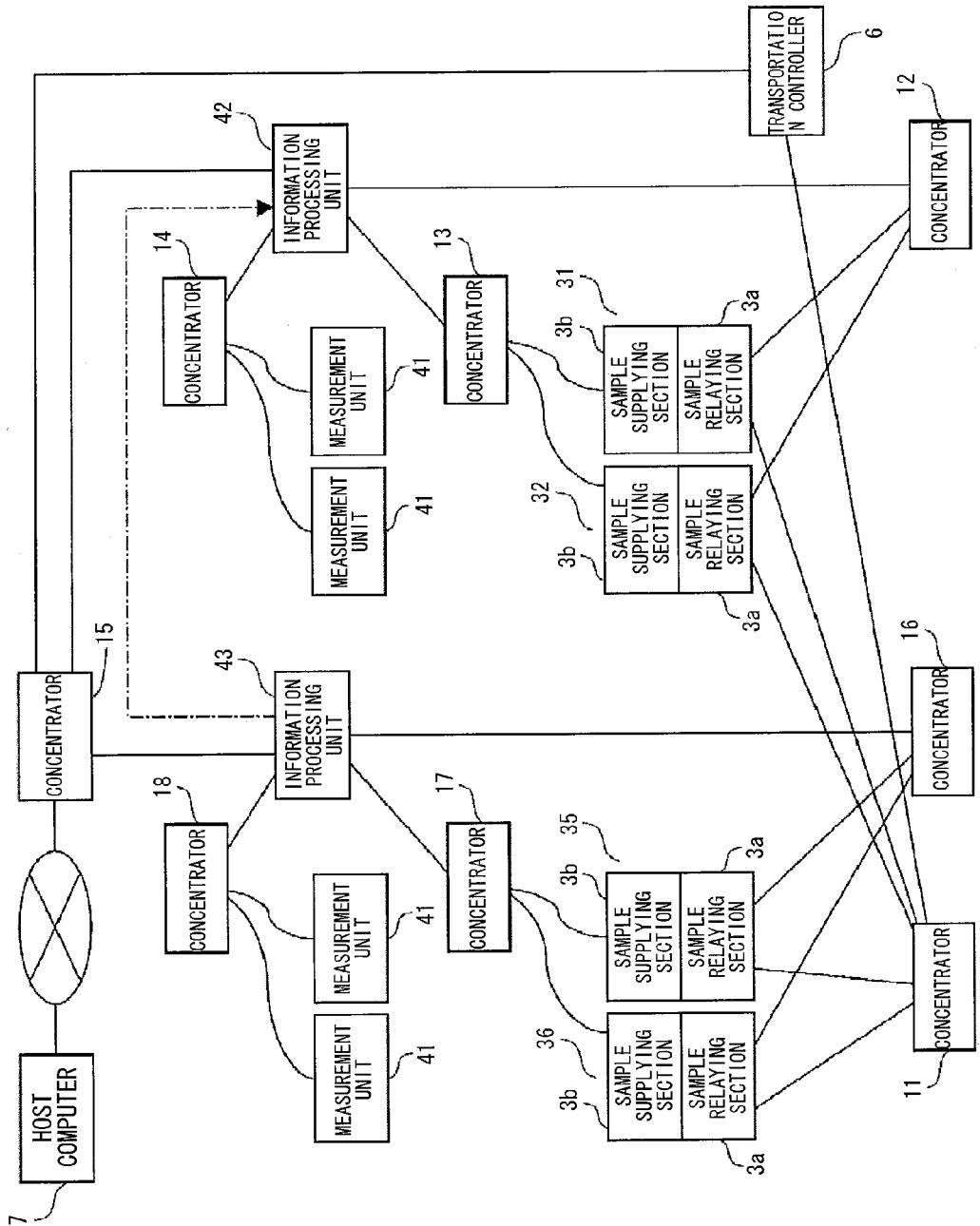
FIG. 14 schematically shows mutual connection relationship between units and apparatuses in a modification of a sample processing system according to an embodiment.

FIG. 14 schematically shows mutual connection relationship between units and apparatuses of the sample processing system at a time when four measurement units 41 are controlled by two information processing units.

The sample processing system in this case is equivalent to the sample processing system 1 of the above embodiment (see FIG. 3) from which one measurement unit 41 controlled by the information processing unit 42 and the transporting unit 33 are omitted, and to which an information processing unit 43, two measurement units 41 controlled by the information processing unit 43, transporting units 35 and 36, and concentrators 16 to 18 are added. It should be noted that in FIG. 14, the loading unit 21, the preprocessing unit 22, the collection unit 23, the transporting unit 34, the smear preparing apparatus 5 are not shown for convenience. Hereinafter, differences between FIG. 14 and FIG. 3 will be described.

With reference to FIG. 14, sample relaying sections 3a of the transporting units 35 and 36 are communicably connected to the concentrator 11. The sample relaying sections 3a of the transporting units 35 and 36, and the information processing unit 43 are communicably connected to a concentrator 16. Sample supplying sections 3b of the transporting units 35 and 36, and the information processing unit 43 are communicably connected to a concentrator 17. Two measurement units 41 corresponding to the transporting units 35 and 36, and the information processing unit 43 are communicably connected to a concentrator 18. The information processing unit 43 is communicably connected to the concentrator 15. Further, an analog audio signal outputted from the information processing unit 43 is inputted to the information processing unit 42, as shown in a long chain line in FIG. 14.

Also in this case, the menu screen A1 and other screens for the computer 420 of the information processing unit 42, and the menu screen and other screens for the computer of the information processing unit 43 are displayed on the display input unit 426 of the information processing unit 42. Further, by means of the screen switching button A11 provided in the menu screen A1 for the computer 420 of the information processing unit 42 and the screen switching button provided in the menu screen for the computer of the information processing unit 43, the menu screen displayed on the display input unit 426 is switched.

Similarly, by means of the screen switching button A11 provided on screens for the computer 420 of the information processing unit 42 other than the menu screen A1, and the screen switching button provided on screens for the computer of the information processing unit 43 other than its menu screen, the screen displayed on the display input unit 426 is switched.

Also in this case, when the screen on the display input unit 426 is to be switched, processes by the information processing units 42 and 43 are performed in a similar manner to that described above. That is, as shown in FIG. 15A, the computer 420 of the information processing unit 42 performs processes similar to those shown in FIG. 11A. However, in each step, the connection destination for the remote desktop application is changed to the computer of the information processing unit 43. Further, as shown in FIG. 15B, the computer of the information processing unit 43 performs processes similar to those shown in FIG. 11B. In this case, in each step, the connection source for the remote desktop application is the computer 420 of the information processing unit 42, as in the case of FIG. 11B.

In the above embodiment, the display input unit 426 of the information processing unit 42 is implemented by a touch-sensitive display. Instead, the display input unit 426 of the information processing unit 42 may be implemented by an input unit composed of a mouse or a keyboard, and a display unit composed of a display.

Further, in the above embodiment, the screen switching buttons A11 and B11 are always displayed at a predetermined position in screens for the computer 420 of the information processing unit 42 (such as the menu screen A1) and screens for the computer 600 of the transportation controller 6 (such as the menu screen B1). However, the screen switching buttons A11 and B11 may be displayed on a different position from the above predetermined position.

Further, in the above embodiment, the sample processing system 1 is configured such that the information processing unit 42 includes the display input unit 426 and the speaker 427, and the transportation controller 6 does not include a display input unit and a speaker. However, the present invention is not limited thereto. The sample processing system 1 may be configured such that the transportation controller 6 includes a display input unit and a speaker, and the information processing unit 42 does not include a display input unit and a speaker. In this case, a screen for the computer 420 of the information processing unit 42 (such as the menu screen A1) and a screen for the computer 600 of the transportation controller 6 (such as the menu screen B1) are displayed on the display input unit of the transportation controller 6, and operations are performed via the display input unit.

Figure 16A:
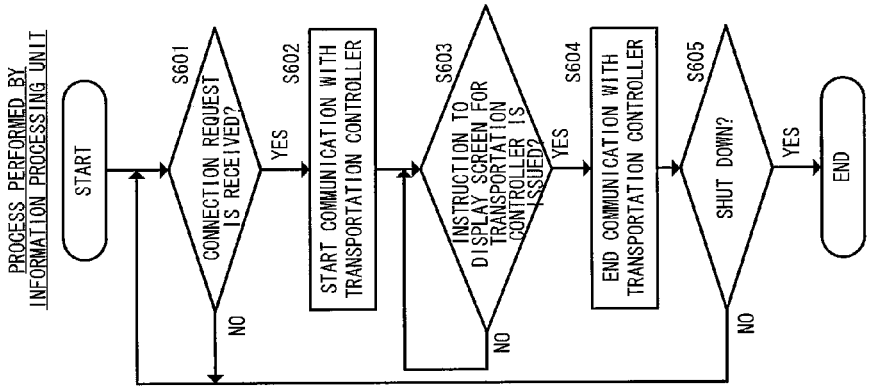
FIG. 16A and FIG. 16B are flow charts showing processes performed by a computer of a transportation controller and by a computer of an information processing unit when screens are switched in a modification of a sample processing system according to an embodiment, respectively.
Figure 16B:
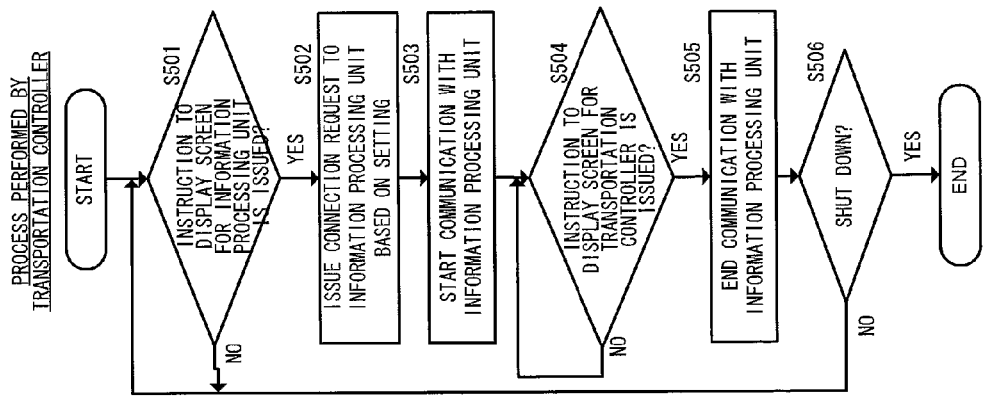

Also in this case, when the screen on the display input unit is to be switched, processes by the computer 600 of the transportation controller 6 and the computer 420 of the information processing unit 42 are performed in a similar manner to that described above. That is, as shown in FIG. 16A, the computer 600 of the transportation controller 6 performs processes similar to those shown in FIG. 11A. Further, as shown in FIG. 16B, the computer 420 of the information processing unit 42 performs processes similar to those shown in FIG. 11B. In this case, since the transportation controller 6 includes the display input unit, the computer 600 of the transportation controller 6 serves as the connection source for the remote desktop application, and the computer 420 of the information processing unit 42 serves as the connection destination for the remote desktop application. Therefore, in S501 to S506 and S601 to S605 shown in FIG. 16A and FIG. 16B, compared with those shown in FIGS. 11A and B, the connection source for the remote desktop application is changed from the computer 420 of the information processing unit 42 to the computer 600 of the transportation controller 6, and the connection destination for the remote desktop application is changed from the computer 600 of the transportation controller 6 to the computer 420 of the information processing unit 42.

Further, in the above embodiment, in order to cause the display input unit 426 to display a screen for the computer 600 of the transportation controller 6 (such as the menu screen B1), the remote desktop application of Microsoft Corporation is used. However, another type of software which realizes similar functions, for example, "pcAnywhere" of Symantec Corporation, may be used.

Further, in the above embodiment, the remote desktop application and a computer program for displaying screens for the computer 420 of the information processing unit 42 (such as the menu screen A1) and the setting screen A100 are stored in the hard disk 425 of the information processing unit 42 in advance. However, the present invention is not limited thereto. Alternatively, a CD, a DVD, or the like in which these computer programs are stored may be read by the readout device 424, and these computer programs may be stored in the hard disk 425. Similarly, in the above embodiment, the remote desktop application and a computer program for displaying screens for the computer 600 of the transportation controller 6 (such as the menu screen B1) and the setting screen B100 are stored in the hard disk 605 of the transportation controller 6 in advance. However, the present invention is not limited thereto. Alternatively, a CD, a DVD, or the like in which these computer programs are stored may be read by the readout device 604, and these computer programs may be stored in the hard disk 605.

Further, in the above embodiment, when the screen switching button A11 is touched, communication using the remote desktop application is started between the computer 420 of the information processing unit 42 and the computer 600 of the transportation controller 6, and when the screen switching button B11 is touched, the communication using the remote desktop application is ended. However, the present invention is not limited thereto. When the screen switching button A11 is touched first, communication using the remote desktop application may be started, and then, when the screen switching button B11 is touched, a screen for the computer 600 of the transportation controller 6 (such as the menu screen B1) may disappear from the display input unit 426 without ending the communication using the remote desktop application. In this case, when the screen switching button A11 is touched again, the screen for the computer 600 of the transportation controller 6 (such as the menu screen B1) which has disappeared may be displayed again on the display input unit 426.

Further, in the above embodiment, only the screens for the information processing unit 42 and the transportation controller 6 are displayed on the display input unit 426. However, the present invention is not limited thereto. For example, in a case where other units (apparatuses), such as other information processing units, are included in the sample processing system 1, screens for such other units (apparatuses) may be displayed on the display input unit 426 of the information processing unit 42. In this case, the screen switching buttons are provided, for example, for respective units (apparatuses) for which screens can be switched, or a pull-down menu that lists units (apparatuses) for which screens can be switched is displayed such that a unit (apparatus) can be selected therefrom when one screen switching button is operated. Moreover, for example, audio signals outputted from a plurality of units (apparatuses) are inputted in parallel, to the audio input terminal of the audio interface 423 of the information processing unit 42. In this case, when an error has occurred in any of the units (apparatuses), the error notification dialog A40 is displayed. However, since the units (apparatuses) cannot be identified from the audio signals, the unit (apparatus) where the error has occurred cannot be identified from the error notification dialog A40. Therefore, the user needs to confirm in which unit (apparatus) the error has occurred, by sequentially switching the screen by operating the screen switching button.

In this case, by differentiating the audio signals outputted by units (apparatuses) from each other, the units (apparatuses) may be identified by the audio signals. The controller 421 of the information processing unit 42 discriminates the difference among the audio signals, determines from which unit (apparatus) the audio signal has been outputted, and identifies the unit (apparatus) where the error has occurred by means of the error notification dialog A40. In this manner, the user can immediately know the unit (apparatus) in which the error has occurred. Instead of using different audio signals for respective units (apparatuses), an error may be notified of for each unit (apparatus) through communication with the communication interface 422.

Further, in the above embodiment, even when a screen for the computer 420 of the information processing unit 42 (such as the menu screen A1) is being displayed on the display input unit 426, the computer 420 of the information processing unit 42 monitors whether the computer 600 of the transportation controller 6 has detected an abnormality in transporting operations performed by the transporting units 31 to 33 or an abnormality in the communication with the host computer 7, and when an abnormality has been detected, the computer 420 of the information processing unit 42 causes the display input unit 426 to display the error notification dialog A40. However, the present invention is not limited thereto. For example, in a configuration where a sample amount detection sensor which detects the amount of a sample in a sample container is provided in the preprocessing unit 22, when a screen for the computer 420 of the information processing unit 42 is being displayed on the display input unit 426, the computer 420 of the information processing unit 42 monitors whether the computer 600 of the transportation controller 6 has detected a shortage of the amount of a sample in a sample container, and when a shortage of the amount of a sample has been detected, the message indicating the shortage may be displayed on the display input unit 426. Accordingly, it is possible to urge the user to switch the screen to a screen for the computer 600 of the transportation controller 6, and to allow the user to confirm the sample container where the shortage of the amount of the sample has occurred.

Further, in the above embodiment, information processing concerning the measurement units 41 performed by the computer 420 of the information processing unit 42 includes a process of transmitting an instruction to start sample measurement operations to the measurement units 41, a process of analyzing data of the samples detected by the measurement units 41, and the like. However, the present invention is not limited thereto. The information processing performed by the computer 420 may include a process of setting a condition for sample processing operations performed by the measurement units 41.

Further, in the above embodiment, an example of a screen for each computer includes a menu screen and screens sequentially followed from the menu screen. However, such a screen may be any screen outputted from the computer, and may be, for example, a desktop screen outputted form the computer.

Further, in the above embodiment, when a switching instruction is accepted while a screen for the computer 420 of the information processing unit 42 (such as the menu screen A1) is being displayed on the display input unit 426, the screen for the computer 420 is caused to disappear from the display input unit 426 and a screen for the computer 600 of the transportation controller 6 (such as the menu screen B1) is displayed. However, the present invention is not limited thereto. For example, when a switching instruction is accepted while a screen for the computer 420 is being displayed, a screen for the computer 600 may be displayed on top of the screen for the computer 420.

Further in the above embodiment, when the screen switching button A11 is touched, a screen for the computer 420 being displayed on the display input unit 426 is switched to a screen for the computer 600. However, the present invention is not limited thereto. For example, when a screen for the computer 420 is double-clicked by use of a mouse or the like, the screen may be switched to a screen for the computer 600.

In addition to the above, various modifications of the embodiments of the present invention may be made without departing from the scope of the technical idea defined by the claims.

What is claimed is:

1. A sample processing system that performs a sample processing operation and a sample transporting operation, comprising:
 a sample processing apparatus configured to process a sample in a sample container; a transporting apparatus configured to transport the sample container to the sample processing apparatus;
 a first computer system configured to collect first status information on the sample processing operation and control the sample processing operation;
 a second computer system independent from the first computer system and configured to collect second status information on the sample transporting operation and control the sample transporting operation;
 a communication network that connects the first and second computer systems for data communication between them; and
 a display unit physically connected to the first computer system,
 wherein the first computer system is programmed to:
 generate and display on the display unit a first menu screen for controlling the sample processing operation, the first menu screen comprising (i) a first non-transitional screen showing a computer switching button at a fixed location of the display unit and (ii) a first transitional screen showing the first status information;
 responsive to an operation of the computer switching button on the first menu screen, send a connection request to the second computer system and then connect to the second computer system via the communication network;
 via the communication network, receive from the second computer system and display on the display unit a second menu screen for controlling the sample transporting operation, the second menu screen comprising (i) a second non-transitional screen showing the computer switching button at the fixed location of the display unit and (ii) a second transitional screen showing the second status information;
 responsive to an operation of the computer switching button on the second menu screen, send switching button operation information to the second computer system via the communication network; and
 responsive to the operation of the computer switching button on the second menu screen, end the data communication with the second computer system and switch the second menu screen to the first menu screen on the display unit, and
 wherein the second computer system is programmed to:
 receive the connection request from the first computer system and connect to the first computer system via the communication network;
 after connecting to the first computer system, output the second menu screen and the second status information to the first computer system via the communication network; and
 responsive to receipt of the switching button operation information from the first computer system, end the data communication with the first computer system.

2. The sample processing system of claim 1, wherein the first transitional screen displays buttons for controlling the sample processing operation.

3. The sample processing system of claim 1, wherein the second transitional screen displays buttons for controlling the sample transporting operation.

4. The sample processing system of claim 1, wherein the first and second computer systems are arranged side by side in one container.

5. The sample processing system of claim 1, wherein the display unit comprises a touch panel display.

6. The sample processing system of claim 1, wherein the first status information includes an error status of the sample processing operation, and the second status information includes an error status of the sample transporting operation.

7. The sample processing system of claim 6, wherein the second computer system is programmed to send updated second status information to the first computer system via the communication network when it has detected an error in the sample transporting operation, and the first computer system is programmed to show, in response to receipt of the updated second status information from the second computer system, the first computer system shows an error notice on over the first menu screen on the display unit if the first computer system shows the first menu screen on the display.

8. The sample processing system of claim 7, wherein the first computer system includes a first audio terminal, and the second computer system includes a second audio terminal connected to the first audio terminal via a cable, and further wherein the second computer system is programmed to output an audio signal from the second audio terminal to the first audio terminal via the cable when the second computer system has detected an error in the sample transporting operation, and in response to receipt of the audio signal from the second computer system via the first audio terminal, the first computer system shows an error notice over the first menu screen on the display unit if the first computer system shows the first menu screen on the display.

9. The sample processing system of claim 1, wherein the sample processing operation includes an operation of measuring a sample by using a reagent, and the first transitional screen shows a button to be operated to replace the reagent.

10. The sample processing system of claim 1, wherein the first status information includes an error status of the sample processing operation, and the first computer system is programmed to show an error notice on the first menu screen if the first status information indicates that an error has occurred in the sample processing operation.

11. The sample processing system of claim 1, wherein the sample transporting operation includes an operation of controlling a plurality of transporting units, and the second status information includes an error status of the plurality of transporting units, and further wherein the second transitional screen shows the second status information on the display unit in such a manner that the second transitional screen shows the plurality of transporting units in a geometric layout thereof, along with a notice displayed to identify a transporting unit among the plurality of transporting units as having an error as reported by the error status included in the second status information.

12. The sample processing system of claim 1, wherein the sample processing operation comprises an operation of measuring a sample to obtain measurement data, and an operation of analyzing the measurement data.

13. The sample processing system of claim 12, wherein the operation of measuring the sample comprises an operation of measuring blood, and the measurement data includes characteristic data reflecting characteristic of blood cells in the blood, and further wherein the first computer system counts blood cells based on the characteristic data.

14. The sample processing system of claim 1, wherein the first status information includes an error status of the sample processing operation, and when the first computer system has detected an error in the sample processing operation while it shows the second menu screen on the display unit, the first computer system shows an error notice of the sample processing operation over the second menu screen.

15. The sample processing system of claim 14, wherein the sample processing operation includes an operation of processing a sample by using a reagent, and the error status information includes a shortage of the reagent in the sample processing operation.

16. The sample processing system of claim 1, wherein the sample processing operation includes operating a plurality of the sample processing apparatuses, and the sample transporting operation includes an operation of transporting sample containers to their destination sample processing apparatuses, each of the sample containers having an identification information examined in the sample transporting operation, and further wherein the second computer system determines a destination sample processing apparatus for each sample container, based on the examined identification information, and the sample transporting operation includes an operation of transporting the sample containers to the determined destination sample processing apparatuses.

17. A sample processing system that performs a sample processing operation and a sample transporting operation, comprising:

a sample processing apparatus configured to process a sample in a sample container; a transporting apparatus configured to transport the sample container to the sample processing apparatus;

a first computer system configured to collect first status information on the sample processing operation and control the sample processing operation;

a second computer system independent from the first computer system and configured to collect second status information on the sample transporting operation and control the sample transporting operation;

a communication network that connects the first and second computer systems for data communication between them; and a display unit physically connected to the second computer system, wherein the second computer system is programmed to:

generate and display on the display unit a second menu screen for controlling the sample transporting operation, the second menu screen comprising (i) a second non-transitional screen showing a computer switching button at a fixed location of the display unit and (ii) a second transitional screen showing the second status information;

responsive to an operation of the computer switching button on the second menu screen, send a connection request to the first computer system and then connect to the first computer system via the communication network;

via the communication network, receive from the first computer system and display on the display unit a first menu screen for controlling the sample processing operation, the first menu screen comprising (i) a first non-transitional screen showing the computer switching button at the fixed location of the display unit and (ii) a first transitional screen showing the first status information;

responsive to an operation of the computer switching button on the second menu screen, send switching button operation information to the first computer system via the communication network; and responsive to the operation of the computer switching button on the first menu screen, end the data communication with the first computer system and switch the first menu screen to the second menu screen on the display unit, and further wherein the first computer system is programmed to:

receive the connection request from the second computer system and connect to the second computer system via the communication network;

after connecting to the second computer system, output the first menu screen and the first status information to the second computer system via the communication network; and responsive to receipt of the switching button operation information from the second computer system, end the data communication with the second computer system.

* * * * *